(12) United States Patent
Yu et al.

(10) Patent No.: US 10,070,602 B2
(45) Date of Patent: Sep. 11, 2018

(54) MARKERS ASSOCIATED WITH SOYBEAN RUST RESISTANCE AND METHODS OF USE THEREFOR

(71) Applicant: Syngenta Participations AG, Basel (CH)

(72) Inventors: Ju-Kyung Yu, Slater, IA (US); Glenn Bowers, Bay, AR (US); Becky Welsh Breitinger, Research Triangle Park, NC (US); Nanda Chakraborty, Research Triangle Park, NC (US)

(73) Assignee: Syngenta Participations AG, Basel (CH)

( * ) Notice: Subject to any disclaimer, the term of this patent is extended or adjusted under 35 U.S.C. 154(b) by 241 days.

(21) Appl. No.: 14/872,443

(22) Filed: Oct. 1, 2015

(65) Prior Publication Data

US 2016/0073598 A1 Mar. 17, 2016

Related U.S. Application Data

(60) Division of application No. 12/690,782, filed on Jan. 20, 2010, which is a continuation of application No. PCT/US2009/051003, filed on Jul. 17, 2009.

(60) Provisional application No. 61/153,495, filed on Feb. 18, 2009, provisional application No. 61/081,989, filed on Jul. 18, 2008.

(51) Int. Cl.
| | |
|---|---|
| *C12N 15/82* | (2006.01) |
| *C12Q 1/68* | (2018.01) |
| *A01H 5/10* | (2018.01) |
| *A01H 1/04* | (2006.01) |
| *C12Q 1/6895* | (2018.01) |

(52) U.S. Cl.
CPC ............ *A01H 1/04* (2013.01); *A01H 5/10* (2013.01); *C12N 15/8282* (2013.01); *C12Q 1/6895* (2013.01); *C12Q 2600/13* (2013.01); *C12Q 2600/156* (2013.01); *Y10T 436/143333* (2015.01)

(58) Field of Classification Search
None
See application file for complete search history.

(56) References Cited

U.S. PATENT DOCUMENTS

| | | | |
|---|---|---|---|
| 4,458,066 | A | 7/1984 | Caruthers et al. |
| 2006/0137039 | A1 | 6/2006 | Sebastian |
| 2006/0288444 | A1 | 12/2006 | McCarroll |
| 2011/0185448 | A1 | 7/2011 | Yu et al. |

FOREIGN PATENT DOCUMENTS

| | | |
|---|---|---|
| WO | 2008/054546 | 5/2008 |
| WO | 2009/079729 | 7/2009 |
| WO | 2010/009404 | 1/2010 |
| WO | 2010/096227 | 8/2010 |

OTHER PUBLICATIONS

Funke, R.P., et al., 1993, Plant Molecular Biology 22: 437-446.*
Choi I.Y., et al., 2007, Genetics 176: 685-696, with Supplemental Data File.*
Hartwig, E.E., 1983, Crop Science 26: 1135-1136.*
Murata, M., and Thompson, P.E. (1976) Biochemical Genetics 14: 183-195.*
Kreitman, M. (1983) Nature 304: 412-417.*
Silva et al. (2008) Theoretical and Applied Genetics 117: 57-63.*
Anderson et al., "Development of simple sequence repeat markers for the soybean rust funus, *Phakopsora pachyrhizi*," Molecular Ecology Resources. (2008). vol. 8: 1310-1312.
Bromfield, K.R. and Hartwig, E.E., "Resistance to soybean rust and mode of inheritance," Crop Science. (1980) vol. 20(2): 254-255.
Calvo et al., "Two major recessive soybean genese conferring soybean rust resistance," Crop Science (2008), 28(4): 1350-1354.
Garcia et al., "Molecular mappnig of soybean rust (*Phakopsora pachyrhizi*) resistance genes: discovery of a novel locus and alleles," Theoretical and Applied Genetics (2008). vol. 117: 545-553.
Hartman et al., "Breeding for Resistance to Soybean Rust," (2005), Plant Disease, 89(6):664-666.
Hartwig and Bromfield, "Relationships among three genes conferring specific resistance to rust in soybeans," (1983). Crop Science, vol. 23: 237-239.
Hartwig, E.E., "Identification of a fourth major gene conferring resistance to soybean rust," (1983). Crop Science, vol. 23: 237-239.
Hyten et al., "Map Location of the Rpp1 Locus that confers resistance to soybean rust in soybean," (2007), Crop Science. 47(2): 837-840.
Hyten et al., "High-throughput genotyping with the GoldeGate assay in the complex genome of soybean," (2008). Theoretical and Applied Genetics vol. 116: 945-982.
McLean, R.J.and Bythe, D. "Inheritance ofresistance to rust (Phakopsora pachyrhizi) in soybean," (1980). Aust. J. Ahric. Res. vol. 31: 951-956.
Miles et al., "Evaluation of Soybean Germplasm for Resistance to Phakospora pachyrhizi," Plant Health Progress. Accessed on Feb. 15, 2013, 25 pages.
Monteros et al., "Mapping and Confirmation of the 'Hyuuga' Red-Brown Lesion Resistance Gene for Asian Soybean Rust," (2007). Crop Science. Vo. 47: 829-836.
Notification Concerning Transmittal of International Preliminary Report on Patentability (Chapter 1 of the Patent Cooperation Treaty) corresponding to International Patent Application No. PCT/US2010/021523 dated Sep. 1, 2011.

(Continued)

*Primary Examiner* — Amjad Abraham
*Assistant Examiner* — Bratislav Stankovic
(74) *Attorney, Agent, or Firm* — Kevin Markham

(57) ABSTRACT

Methods for conveying soybean rust (SBR) resistance into non-resistant soybean germplasm are provided. In some embodiments, the methods include introgressing SBR resistance into a non-resistant soybean using one or more nucleic acid markers for marker-assisted breeding among soybean lines to be used in a soybean breeding program, wherein the markers are linked to and/or associated with SBR resistance. Also provided are single nucleotide polymorphisms (SNPs) associated with resistance to SBR; soybean plants, seeds, and tissue cultures produced by any of the disclosed methods; seed produced by the disclosed soybean plants; and compositions including amplification primer pairs capable of initiating DNA polymerization by a DNA polymerase on soybean nucleic acid templates to generate soybean marker amplicons.

6 Claims, 5 Drawing Sheets

Specification includes a Sequence Listing.

(56) References Cited

OTHER PUBLICATIONS

Notification of Transmittal of the International Search Report and the Written Opinion of the International Searching Authority, or the Declaration corresponding to International Patent Application No. PCT/US2009/051003 dated Feb. 5, 2010; and International Preliminary Report on Patentability dated Apr. 29, 2011.
Notification of Transmittal of the International Search Report and the Written Opinion of the International Searching Authority, or the Declaration corresponding to International Patent Application No. PCT/US2010/021523 dated Mar. 30, 2010.
Official Action corresponding to U.S. Appl. No. 13/054,760 dated Apr. 23, 2013.
Official Action corresponding to U.S. Appl. No. 13/054,760 dated Oct. 24, 2012.
Ray et al., "Genetics and mapping of adult plant rust resistance in soybean PI 587886 and PI 587880A," (2009). Theoretical and Applied Genetics, vol. 119 pp. 271-280.
Ribeiro et al., "Genetic control of Asian rust in soybean," (2007). Euphytica, vol. 157, pp. 15-25.
Silva et al., "Molecular mapping of two loci that confer resistance to Asian rust in soybean," (2008). Theoretical and Applied Genetics. vol. 117, pp. 57-63.
Zhu et al., "Single-nucleotide polymorphisms in soybean," (2003). Genetics, vol. 163, pp. 1123-1134.
Choi et al., Genetics, 2007 176:685-696, Supplemental Data File (58 additional pages disclosing consensus soybean genetic map).
Hyten, D.L. "Mappying soybean rust single gene resistance," Proc. 2007 Natl. Soybean Rust Symp, Louisville, KY (Dec. 12-14, 2007).

\* cited by examiner

| MARKER NAME | MAP POSITION | MARKER TYPE |
|---|---|---|
| Sat_255 | 48.738 | SSR |
| SEQ ID NO: 4 | 49.858 | SNP |
| Satt620 | 53.705 | SSR |
| SEQ ID NO: 5 | 57.697 | SNP |
| Sat_350 | 60.717 | SSR |
| SEQ ID NO: 6 | 60.927 | SNP |

| MARKER NAME | MAP POSITION | MARKER TYPE |
|---|---|---|
| Sat_275 | 32.488 | SSR |
| SEQ ID NO: 11 | 34.26 | SNP |
| SEQ ID NO: 12 | 34.27 | SNP |
| Sat_280 | 35.188 | SSR |
| SEQ ID NO: 13 | 38.8 | SNP |

SEQUENCE LISTING

```
<160> NUMBER OF SEQ ID NOS: 94

<210> SEQ ID NO 1
<211> LENGTH: 459
<212> TYPE: DNA
<213> ORGANISM: Glycine max
<220> FEATURE:
<221> NAME/KEY: misc_feature
<222> LOCATION: (428)..(428)
<223> OTHER INFORMATION: r is a or g

<400> SEQUENCE: 1
ttttgatcca aaacaaagct gaaaagaaag gggacaggta tgaagcaatc ttcagcttct      60
actttggaga ctatggtcac atagcagtgc agggaccttac cctgacctat gaggacacat    120
atttggctgt gactggtggg tctggcatat ttgagggtgt taaaggtcaa gtgaagctgc    180
gtcagattgt gtatcctttc aagattttgt acacatttta tctaaagggt atcaaggatt    240
tgcctcagga gcttcttgtc aagactgttg agccaattcc atctgttgaa ccttcccctg    300
ctgctaaggc ccttgagccc aatgctacca ttgctggctt caccgactaa ttcatcaact    360 tttttttgtat ttgctttggc ctttgtagta gtatgattta agttactgaa taataataac    420
aagtgggrac tatgatgggt tttgtagtgg tggagtttc                            459

<210> SEQ ID NO 2
<211> LENGTH: 1101
<212> TYPE: DNA
<213> ORGANISM: Glycine max
<220> FEATURE:
<221> NAME/KEY: misc_feature
<222> LOCATION: (255)..(932)
<223> OTHER INFORMATION: r is a or g
<220> FEATURE:
<221> NAME/KEY: misc_feature
<222> LOCATION: (267)..(267)
<223> OTHER INFORMATION: s is c or g

<400> SEQUENCE: 2
ttacaccaga atcatggcca ccaatcaaat accctatca tcttattaca gaaaagggga      60
taagagaagg ggaaaaaaaa tctctagaaa ctgaagaatc aaggtttggt tcaaaaactg    120
tgcagttgcg ttagcatgtg aacaagctca tcactagaag gcctatctgc aggcatatca    180
gagaggcatg cagcagcaat cctaaccgcc attagcatct catcttcctc accttcttcc    240
cctaacatgc tcttrtctag agcttcstgc gcctcgcccg cttgctgcaa gtgtctcagc    300
caacatccca aacttccccc actggctgct tctccaaaga atggatctgt aggatcctta    360
ccagttaaca aaacacctag tatcatgcca aaactaaaga tgtcactttt gtcagtgtac    420
ctgctgaaat tgccaaaaaa caccattcaa tctgaatacc atgaagctcc acatatacaa    480
gaatggaatg aagttaaaat aaacatctta ttggcaatac catcccata tatgcaatgc    540 catcaatcaa gcaatctttt attgttatta cttattgcta ttgatattga tgcatccaga    600
tatacaccac tgaaaaacta gaagtattcc aagttaaatt aggaaaaaaa acctttgtca    660
attattatta taatttagtt gtggtctcac tcaccaatct aggtttagta gtttgcagca    720
tgtgaactat aaactatatt attcatttgg accagactta gtgccaactg cctaaggtct    780
```

-continued

| aaaacttgac atcaggaagt aatgggtagt tacaaaaaca aatagcaaag tctttattaa | 840 |
| ataataccaa attcaatcag caaatgatac aatgacaata cagattacag aatartaatt | 900 |
| tcgtttcaaa acaagagtct ttcattaggg trctacaaag ggggcaaaaa accaatgagg | 960 |
| tgtggagctt tgaaaaggt aacgaatcaa acaaattccc aatatcaacc acctaattag | 1020 |
| cctattggtg taaaaaagtg aaagaacaga aacagactaa gggaaaacac tagtgaatga | 1080 |
| gtatgattga aatttgtctt a | 1101 |

```
<210> SEQ ID NO 3
<211> LENGTH: 433
<212> TYPE: DNA
<213> ORGANISM: Glycine max
<220> FEATURE:
<221> NAME/KEY: misc_feature
<222> LOCATION: (1)..(433)
<223> OTHER INFORMATION: r is a or g
<220> FEATURE:
<221> NAME/KEY: misc_feature
<222> LOCATION: (1)..(433)
<223> OTHER INFORMATION: y is c or t

<400> SEQUENCE: 3
```

| ttgggagcca acctgagggg actcagttac gcaagttttg aagctgttgg ttatgayttt | 60 |
| aatgacatgg ctctaggtga acttgtggaa aggrttttrg cttgcttttg tccagcagag | 120 |
| ttttctgttg ctttgcacat tgacatgcat ggtgagaaac ttaataaatt tcccttrgac | 180 |
| aycaaaggat actactgtgg tgagaggagc actgaagagc ttggagtagg tggtgcagtt | 240 |
| gtgtaccaaa catttgttca aggctgcgat ggtagtgcat ctcctaggtc tattctgaaa | 300 |
| tgctgctgga gtgaggacga gaacgaagat gaagtgaggg agatataagt acttctggtt | 360 |
| tttatgttct gttgttattt atctttactg tcgagtgtgt tattacctaa ataaataaat | 420 |
| atggngggtc gca | 433 |

```
<210> SEQ ID NO 4
<211> LENGTH: 471
<212> TYPE: DNA
<213> ORGANISM: Glycine max
<220> FEATURE:
<221> NAME/KEY: misc_feature
<222> LOCATION: (1)..(471)
<223> OTHER INFORMATION: r is a or g

<400> SEQUENCE: 4
```

| ccctatcctc aaatacaagt ccctgatctc atcataccta agttgttaaa gaaaatctag | 60 |
| cccattccat ataaatctta ttaataccctt actccaggac ctgaaagaca acctacccaa | 120 |
| ctatcattaa acaatttagt ctataccacc tatgcccaaa tagatataga tatatagaaa | 180 |
| caaaccaggt ggaagaggaa taacagagaa gtrtataaaa taaatatgca acttcagact | 240 |
| tgtatgctca agccgcaagc ttatatttga agatgtctat cccacaattc cagatccacc | 300 |
| taaacaagaa taaaaatcca caaaacatta gaagcgaatt cgctgctgca aattagaata | 360 |
| taaaattctt aaaaataatc cttaccaaaa gattcatcac attaataata gtatccatgc | 420 |
| ccatgtgagc catcaccccc rtaataagat gaatatgaac ctctaccata a | 471 |

```
<210> SEQ ID NO 5
<211> LENGTH: 489
<212> TYPE: DNA
<213> ORGANISM: Glycine max
<220> FEATURE:
<221> NAME/KEY: misc_feature
```

```
<222> LOCATION: (1)..(489)
<223> OTHER INFORMATION: m is a or c
<220> FEATURE:
<221> NAME/KEY: misc_feature
<222> LOCATION: (1)..(489)
<223> OTHER INFORMATION: w is a or t

<400> SEQUENCE: 5
atctcaatct gctttgacag atagagagaa ggagaatctt gacaacttag ttgacaagga      60
gtgtgcaacm acagagggta tgatatcgag ccagctcaag ttgaagtctt ctttgtcatc     120
caaagcgtct tctcatcaaa gcatggacaa acatgcaatc cttcgacgta tcaggcaacg     180
caggtttaat aacaaagcca aaaccgctct ggaagctctc ataggcacct cagaagccaa     240
caataccggc actgcccaag aacagaagtg gcttcaactg ggtgactctt tctcatctcc     300
ttaactggaa acacaatctc ccccagtttt gcaacccatc tataaatwcc ctctttagtt     360
tccttcaccc aacaaagtca tcttttccat acgcttgcat ggctaggaaa ggaaatccaa     420
cccgatcttt atcggcatgc ttaagaaatc ccactatgta tctattaact gtagtagacc     480
tggtcggtt                                                             489

<210> SEQ ID NO 6
<211> LENGTH: 794
<212> TYPE: DNA
<213> ORGANISM: Glycine max
<220> FEATURE:
<221> NAME/KEY: misc_feature
<222> LOCATION: (1)..(794)
<223> OTHER INFORMATION: r is a or g
<220> FEATURE:
<221> NAME/KEY: misc_feature
<222> LOCATION: (1)..(794)
<223> OTHER INFORMATION: w is a or t

<400> SEQUENCE: 6
ccaaccacgc tgattcttta ggccatcagt caacccttta ctctggaaac tgctaaggaa      60
tataaacctt gaaccagaca tgtcccctga agagtagaaa aatatcatgt ttcagcagca     120
tggttcaaga aaatttgttc atgtaggcaa aattgatttt gaaagaaatt gattatgcaa     180
aattaatgtt ggttaagatt aatttaaag taatgtgatt tatgtttgaa tatttttat      240 cgtagcaact cagtataact ttttaattc aatgcaaaaa tattcaaagt tattttgact      300
caatcaattc tagattcaat atcaattcct catcattgaa acaaatccca acatgtattt     360
aaaatcacga tagttgatat ttcaacgtaa tttcagaaaa atcaacataa aactaaccac     420
gcatcactta atgcgtgcta gggtgagcat taaaattgat ttcaaataaa attaatttc      480 taaaattggt tttggtaaaa attgattttg aagtgacatg agttatgttt gaacgttttt     540
tattctaaaa gttaataaca aatttcaawt tttttttatc caaagcaaaa gtcatctaaa     600
agttatttga actcgaaatc aaatttaaac tcaaaatcaa ttccttaatg tgaaattaaa     660
catgtgtcca tttacctcaa atcatgttat ccgatatttc aacaagactt taaaraatcc     720
tacgtgaaac caaacatgca cttactagaa taagcagagt gaatagcaga aatacccaga     780
ttgtaagctg caga                                                       794

<210> SEQ ID NO 7
<211> LENGTH: 568
<212> TYPE: DNA
<213> ORGANISM: Glycine max
<220> FEATURE:
<221> NAME/KEY: misc_feature
<222> LOCATION: (1)..(568)
```

<223> OTHER INFORMATION: r is a or g
<220> FEATURE:
<221> NAME/KEY: misc_feature
<222> LOCATION: (1)..(568)
<223> OTHER INFORMATION: w is a or t

<400> SEQUENCE: 7

```
gttttacaca gttgcacaaa gtcataaact tcagtgacca ttttttatat tagcctggca      60
gtaagatggc tatttatttc tgagtgtagt ttgtactgat ttaatggttt tattatatgc     120
ctagactttt ctttgatatc aatatcttat gtcatcttct cttggttgtg gatggtattt     180
ttcttctgtg gtgtawtttg ttaaaccaat gatattgtat attaattact tttgtaattt     240
tgatctagta atctattttc atggctattt taaaatattg tagtgggttg aggggaaaat     300
atttagggaa attatttagg ttgactgtgc cttgcctttt aggaatgcat aacgactttt     360
tttcttctaa cagttgratt atatacttag ctttgtaatt aattttgttt arttattcaa     420
ccgattttt tcccacttta ttagcattta tcatgatctg gttccttcac tatattttgt     480
ttctgctagt gccaattttt tacctcaaga ctttactttt gtagcttttg tgctgtttat     540
ttgtttctgt ggatttgtct cgattcat                                        568
```

<210> SEQ ID NO 8
<211> LENGTH: 503
<212> TYPE: DNA
<213> ORGANISM: Glycine max
<220> FEATURE:
<221> NAME/KEY: misc_feature
<222> LOCATION: (1)..(503)
<223> OTHER INFORMATION: r is a or g
<220> FEATURE:
<221> NAME/KEY: misc_feature
<222> LOCATION: (1)..(503)
<223> OTHER INFORMATION: w is a or t
<220> FEATURE:
<221> NAME/KEY: misc_feature
<222> LOCATION: (1)..(503)
<223> OTHER INFORMATION: y is c or t

<400> SEQUENCE: 8

```
ccgagacgrg tgaggaaatc ctcgaggtgg gtcaaggacc cctcgtgctt gcttgggtcg      60
aacatggagg caacgagagt acaaaatgtt agggacacar taagctggtt ttygaggaac     120
tagtacctcc agcaattcaa taagaagaa gaagaacaaa gagggaaaga gtgaggtaat     180
tggaaatttc attcatgcct tgcttgttat ttacattagt atttataaac ttcctagtaa     240
cagaaagatc ctaggaatat ttgcccataa caaaatttgt acacattgtc ccctaggagc     300
agacaatatc aaccaaggaa attctagaag gtagcctcag ctggtctcac ccwtcttcca     360
aaaacgtact ctttraggta agaaggtttt gtaattcttc tttcgaactt agcttcttcc     420
tgtaccccct catttgcttt tgtgacccct gcccttgcct ctgtttgtaa gctcgtatca     480
acatrttttcc gatacagatg cag                                            503
```

<210> SEQ ID NO 9
<211> LENGTH: 769
<212> TYPE: DNA
<213> ORGANISM: Glycine max
<220> FEATURE:
<221> NAME/KEY: misc_feature
<222> LOCATION: (1)..(769)
<223> OTHER INFORMATION: m is a or c
<220> FEATURE:
<221> NAME/KEY: misc_feature
<222> LOCATION: (1)..(769)
<223> OTHER INFORMATION: r is a or g

```
<220> FEATURE:
<221> NAME/KEY: misc_feature
<222> LOCATION: (1)..(769)
<223> OTHER INFORMATION: s is c or g
<220> FEATURE:
<221> NAME/KEY: misc_feature
<222> LOCATION: (1)..(769)
<223> OTHER INFORMATION: w is a or t
<220> FEATURE:
<221> NAME/KEY: misc_feature
<222> LOCATION: (1)..(769)
<223> OTHER INFORMATION: y is c or t

<400> SEQUENCE: 9
aacagagttg gctataacaa ggttttggat aatgccaagc ccatgaatga tccagatgga      60
aggcactttt catcttttac ttacctgagg cttagttcac ttctcatgga acgacaaaac    120
ttcatagagt ttgaaagatt tgtcaaraga atgcatggta agttgatgaa gaaaatttta    180
aatgtatcty tagcctctaa ttgatttatg aaaatatcta ttaaggaaag aaaatcatcc    240
ctttatctgg ccttgattga atgaatgctc acgtgtcatc tgraaccttc ttactccaca    300
gtcccacact cagtagggta aatgggtaat carcaaaacc ctgaagaccc aaatttcttt    360
cagaggcatg gttcagcaac tgtactaata tcatattgaa ctttggattc cattattcgm    420
tcccactgat agtgttcttt gatccacctw gcactagtct ttttatctga ttggaatcat    480
tttataaata attgaacacg aaasgagtat taatgtcagt tttaagaggt gtacttctct    540
tggagagaaa aacactgaaa ctttaagtag ctgcaaaagt tgttgctatc ttgtgggaca    600
ttgattatat tagggttgat gactgtgtca tttctcattg caggggaagc tgttcttgat    660
cttcaggtat aaccggtggg aaacaaagtc ttgttgaatt tgtatttata agtcccctga    720
caaaatggtt ggggggattct gttatagaat aggagaaata ggattgtta               769

<210> SEQ ID NO 10
<211> LENGTH: 513
<212> TYPE: DNA
<213> ORGANISM: Glycine max
<220> FEATURE:
<221> NAME/KEY: misc_feature
<222> LOCATION: (1)..(513)
<223> OTHER INFORMATION: m is a or c
<220> FEATURE:
<221> NAME/KEY: misc_feature
<222> LOCATION: (1)..(513)
<223> OTHER INFORMATION: r is a or g

<400> SEQUENCE: 10
gagaaagaga agtattgcgc atcatgccca aatgtggcca cactttttcat ctttcttgca     60 ttgatatatg gctgaggaaa caatccacct gtccagtatg ccgtctgccg ttgaaaaact    120
cttccgaaac gaaacatgtg agacctgtga catttaccat gagccaatcc cttgacgagt    180
ctcacacatc agacagaaac gatgmtattg agagatatgt tgaacctaca cctactgcag    240
ccagtaactc tttacaacca acttcaggag aacaagaagc aagrcaatga tcttagagaa    300
ctaaaggggt tgttctgctc aaaaagagaa gaatgtagaa tttctgcttc tatagaggaa    360
tgcttctaat tatagattgg attcaaattc tttgtctgta atatggcctt catattcact    420
tggtggtgta aatatgtttc ctttttgtagc atatgcgggc caaggttttg gtggaatttc    480
ttgcataccg atttgaagtt cttttgtcta tgg                                  513

<210> SEQ ID NO 11
<211> LENGTH: 281
<212> TYPE: DNA
```

```
<213> ORGANISM: Glycine max
<220> FEATURE:
<221> NAME/KEY: misc_feature
<222> LOCATION: (1)..(281)
<223> OTHER INFORMATION: y is c or t

<400> SEQUENCE: 11
atccaccaac accacttcac caccaaagcc tagtggagct gtaactgttt ccagtggcat      60
tggccttttg gtgggtctt tctttgtgtc agcaattatg tytggtttca tgggctaggg     120
aagaggcagt gctgttttt ttttattct ccttttatt aatatgttat tgttttgctg      180
agagtttgtg tgaatttcat catttaatcc agatgtatat ctaatcttga tatgtatctc     240
cttttaatat ttaaaaatga cacatttctt tagctgcttc c                         281

<210> SEQ ID NO 12
<211> LENGTH: 948
<212> TYPE: DNA
<213> ORGANISM: Glycine max
<220> FEATURE:
<221> NAME/KEY: misc_feature
<222> LOCATION: (1)..(948)
<223> OTHER INFORMATION: w is a or t

<400> SEQUENCE: 12 tgaattttg ttatgagagc atctccattt taaagagatt tcgtttctgg gtatcagaaa       60
acacctccct tccgattaga tttctatatt ttgcctagac gtcaaatgca cgatgaattc     120
tttgtatgat gtttgaaaat tgaagtcttc tgtaatacwt gattatcaac ctcaaatttt     180
gatgcgacaa caagttatgc tttgtgaant tgttattgat gattgtatgg tgtgatttgg     240
tttcaggttt gaaacttgtt actgtggacc gtccttttgc tgagaagcac tatgctgatt     300
tgtctgccaa gcctttcttt agtggttgg tggattacat tatctctggc cctgttgttg      360
ccatgatctg ggagggcaag aatgttgtta caactggccg aaagattatn ggagccacaa     420
acccagctca atctgagcct ggaactatcc gtggtgactt tgccattgac attggaaggt     480
atagacttgt tttcatcatc gttcaagcaa gtttacgttt tcaaatcttt tgttttaaca     540
catgaatatg aatctgtttt cattgttgtt catgtttcta atctagtttg gtggatgtta     600
ggttttcatt nttgttgttt gattttcaat ttctcccgaa ttttttttctt atttacaaca    660
ttggtttcca acgttctgtg ttttagagaa aagagtgttg tgctcaacca attctgcgaa    720
tattgcaata tgttcatgac atcatcaatt aagcaagatg ataacactgt tgagtacatc    780
ataatcaagg gagtggaatc caacaaatcc atgttctgta tcttgtattc atgaaaatca    840
aaattgttgg ggtagtcaat gtttatcaac attaaaaggt agtgtgnatc tanatactta    900
ttatttncaa ttctataaag gatttgaagg gaactttgaa ttttttttt               948

<210> SEQ ID NO 13
<211> LENGTH: 485
<212> TYPE: DNA
<213> ORGANISM: Glycine max
<220> FEATURE:
<221> NAME/KEY: misc_feature
<222> LOCATION: (1)..(485)
<223> OTHER INFORMATION: r is a or g

<400> SEQUENCE: 13
ttctatgacc aacctaccgc ctgtgggtaa agctaaacta agttctcaca ggtgaggtga      60
gttcaccaac cacggccgcc agaatttcca gatccccatc cgttccctga tgctgctttc     120
ttgggggcag atccccagcc agagcttcct tgttcaccat cacttggacc agcaccacca     180
```

-continued

```
ctcgcttgtc cccccagcc accattgtca ctgttactag ctccacctcc tcccctccc      240 caaccactac tgcctccacc gcttccacca ccaccacccc aaccaccagg aaaagcttcc    300
cttccaggag aattctgaac cttggcccct ggaaaattgc ttaaaccatc atccgartcc    360
tttgtattat tagaaccca tctgccccca taaccagagt cctgcctttc attattggag     420
ttgtctcctc tattgttata agaacctcga ccacgaccac gtacacgccc ttttccaccc    480
accga                                                                485
```

<210> SEQ ID NO 14
<211> LENGTH: 20
<212> TYPE: DNA
<213> ORGANISM: Glycine max

<400> SEQUENCE: 14

```
aggatttgcc tcaggagctt                                                20
```

<210> SEQ ID NO 15
<211> LENGTH: 22
<212> TYPE: DNA
<213> ORGANISM: Glycine max

<400> SEQUENCE: 15

```
gaaactccac cactacaaaa cc                                             22
```

<210> SEQ ID NO 16
<211> LENGTH: 16
<212> TYPE: DNA
<213> ORGANISM: Glycine max

<400> SEQUENCE: 16

```
agtggggact atgatg                                                    16
```

<210> SEQ ID NO 17
<211> LENGTH: 17
<212> TYPE: DNA
<213> ORGANISM: Glycine max

<400> SEQUENCE: 17

```
agtgggaact atgatgg                                                   17
```

<210> SEQ ID NO 18
<211> LENGTH: 31
<212> TYPE: DNA
<213> ORGANISM: Glycine max

<400> SEQUENCE: 18

```
caatcagcaa atgatacaat gacaatacag a                                   31
```

<210> SEQ ID NO 19
<211> LENGTH: 22
<212> TYPE: DNA
<213> ORGANISM: Glycine max

<400> SEQUENCE: 19

```
agctccacac ctcattggtt tt                                             22
```

<210> SEQ ID NO 20
<211> LENGTH: 19
<212> TYPE: DNA
<213> ORGANISM: Glycine max

<400> SEQUENCE: 20
tttcattagg gtgctacaa                                            19

<210> SEQ ID NO 21
<211> LENGTH: 21
<212> TYPE: DNA
<213> ORGANISM: Glycine max

<400> SEQUENCE: 21
tctttcatta gggtactaca a                                         21

<210> SEQ ID NO 22
<211> LENGTH: 22
<212> TYPE: DNA
<213> ORGANISM: Glycine max

<400> SEQUENCE: 22
caaaagctcc acacctcatt gg                                        22

<210> SEQ ID NO 23
<211> LENGTH: 25
<212> TYPE: DNA
<213> ORGANISM: Glycine max

<400> SEQUENCE: 23
ttgacatcag gaagtaatgg gtagt                                     25

<210> SEQ ID NO 24
<211> LENGTH: 22
<212> TYPE: DNA
<213> ORGANISM: Glycine max

<400> SEQUENCE: 24
ttgaaacgaa attattattc tg                                        22

<210> SEQ ID NO 25
<211> LENGTH: 21
<212> TYPE: DNA
<213> ORGANISM: Glycine max

<400> SEQUENCE: 25
tgttttgaaa cgaaattact a                                         21

<210> SEQ ID NO 26
<211> LENGTH: 23
<212> TYPE: DNA
<213> ORGANISM: Glycine max

<400> SEQUENCE: 26
gggactcagt tacgcaagtt ttg                                       23

<210> SEQ ID NO 27
<211> LENGTH: 21
<212> TYPE: DNA
<213> ORGANISM: Glycine max

<400> SEQUENCE: 27
gtgctcctct caccacagta g                                         21

<210> SEQ ID NO 28
<211> LENGTH: 19
<212> TYPE: DNA
<213> ORGANISM: Glycine max

```
<400> SEQUENCE: 28
aagctgttgg ttatgattt                                              19

<210> SEQ ID NO 29
<211> LENGTH: 18
<212> TYPE: DNA
<213> ORGANISM: Glycine max

<400> SEQUENCE: 29
agctgttggt tatgactt                                               18

<210> SEQ ID NO 30
<211> LENGTH: 20
<212> TYPE: DNA
<213> ORGANISM: Glycine max

<400> SEQUENCE: 30
atcccacaat tccagatcca                                             20

<210> SEQ ID NO 31
<211> LENGTH: 26
<212> TYPE: DNA
<213> ORGANISM: Glycine max

<400> SEQUENCE: 31
ttatggtaga ggttcatatt catctt                                      26

<210> SEQ ID NO 32
<211> LENGTH: 16
<212> TYPE: DNA
<213> ORGANISM: Glycine max

<400> SEQUENCE: 32
agccatcacc cccgta                                                 16

<210> SEQ ID NO 33
<211> LENGTH: 16
<212> TYPE: DNA
<213> ORGANISM: Glycine max

<400> SEQUENCE: 33
agccatcacc cccata                                                 16

<210> SEQ ID NO 34
<211> LENGTH: 23
<212> TYPE: DNA
<213> ORGANISM: Glycine max

<400> SEQUENCE: 34
agtctatacc acctatgccc aaa                                         23

<210> SEQ ID NO 35
<211> LENGTH: 22
<212> TYPE: DNA
<213> ORGANISM: Glycine max

<400> SEQUENCE: 35
ggcttgagca tacaagtctg aa                                          22

<210> SEQ ID NO 36
<211> LENGTH: 20
<212> TYPE: DNA
```

```
<213> ORGANISM: Glycine max

<400> SEQUENCE: 36
aggaataaca gagaagtgta                                              20

<210> SEQ ID NO 37
<211> LENGTH: 22
<212> TYPE: DNA
<213> ORGANISM: Glycine max

<400> SEQUENCE: 37
aggaataaca gagaagtata ta                                           22

<210> SEQ ID NO 38
<211> LENGTH: 25
<212> TYPE: DNA
<213> ORGANISM: Glycine max

<400> SEQUENCE: 38
agagagaagg agaatcttga caact                                        25

<210> SEQ ID NO 39
<211> LENGTH: 22
<212> TYPE: DNA
<213> ORGANISM: Glycine max

<400> SEQUENCE: 39
acgtcgaagg attgcatgtt tg                                           22

<210> SEQ ID NO 40
<211> LENGTH: 16
<212> TYPE: DNA
<213> ORGANISM: Glycine max

<400> SEQUENCE: 40
aggagtgtgc aaccac                                                  16

<210> SEQ ID NO 41
<211> LENGTH: 17
<212> TYPE: DNA
<213> ORGANISM: Glycine max

<400> SEQUENCE: 41
aggagtgtgc aacaaca                                                 17

<210> SEQ ID NO 42
<211> LENGTH: 20
<212> TYPE: DNA
<213> ORGANISM: Glycine max

<400> SEQUENCE: 42
ccccagtttg caacccatct                                              20

<210> SEQ ID NO 43
<211> LENGTH: 23
<212> TYPE: DNA
<213> ORGANISM: Glycine max

<400> SEQUENCE: 43
ccatgcaagc gtatggaaaa gat                                          23

<210> SEQ ID NO 44
<211> LENGTH: 17
```

<212> TYPE: DNA
<213> ORGANISM: Glycine max

<400> SEQUENCE: 44
ctaaagaggg aatttat                                                    17

<210> SEQ ID NO 45
<211> LENGTH: 20
<212> TYPE: DNA
<213> ORGANISM: Glycine max

<400> SEQUENCE: 45
aaactaaaga gggtatttat                                                 20

<210> SEQ ID NO 46
<211> LENGTH: 29
<212> TYPE: DNA
<213> ORGANISM: Glycine max

<400> SEQUENCE: 46
gtgtccattt acctcaaatc atgttatcc                                       29

<210> SEQ ID NO 47
<211> LENGTH: 24
<212> TYPE: DNA
<213> ORGANISM: Glycine max

<400> SEQUENCE: 47
gtaagtgcat gtttggtttc acgt                                            24

<210> SEQ ID NO 48
<211> LENGTH: 18
<212> TYPE: DNA
<213> ORGANISM: Glycine max

<400> SEQUENCE: 48
aagactttaa agaatcct                                                   18

<210> SEQ ID NO 49
<211> LENGTH: 19
<212> TYPE: DNA
<213> ORGANISM: Glycine max

<400> SEQUENCE: 49
caagacttta aaaaatcct                                                  19

<210> SEQ ID NO 50
<211> LENGTH: 22
<212> TYPE: DNA
<213> ORGANISM: Glycine max

<400> SEQUENCE: 50
taaatgctaa taaagtggga aa                                              22

<210> SEQ ID NO 51
<211> LENGTH: 16
<212> TYPE: DNA
<213> ORGANISM: Glycine max

<400> SEQUENCE: 51
aggttgactg tgcctt                                                     16

<210> SEQ ID NO 52

```
<211> LENGTH: 21
<212> TYPE: DNA
<213> ORGANISM: Glycine max

<400> SEQUENCE: 52
agctaagtat ataatccaac t                                              21

<210> SEQ ID NO 53
<211> LENGTH: 22
<212> TYPE: DNA
<213> ORGANISM: Glycine max

<400> SEQUENCE: 53
agctaagtat ataattcaac tg                                             22

<210> SEQ ID NO 54
<211> LENGTH: 25
<212> TYPE: DNA
<213> ORGANISM: Glycine max

<400> SEQUENCE: 54
ggaggcaacg agagtacaaa atgtt                                          25

<210> SEQ ID NO 55
<211> LENGTH: 25
<212> TYPE: DNA
<213> ORGANISM: Glycine max

<400> SEQUENCE: 55
tgaattgctg gaggtactag ttcct                                          25

<210> SEQ ID NO 56
<211> LENGTH: 16
<212> TYPE: DNA
<213> ORGANISM: Glycine max

<400> SEQUENCE: 56
cagcttactg tgtccc                                                    16

<210> SEQ ID NO 57
<211> LENGTH: 17
<212> TYPE: DNA
<213> ORGANISM: Glycine max

<400> SEQUENCE: 57
ccagcttatt gtgtccc                                                   17

<210> SEQ ID NO 58
<211> LENGTH: 22
<212> TYPE: DNA
<213> ORGANISM: Glycine max

<400> SEQUENCE: 58
gaacatggag gcaacgagag ta                                             22

<210> SEQ ID NO 59
<211> LENGTH: 29
<212> TYPE: DNA
<213> ORGANISM: Glycine max

<400> SEQUENCE: 59
ttcttcttta ttgaattgct ggaggtact                                      29
```

```
<210> SEQ ID NO 60
<211> LENGTH: 16
<212> TYPE: DNA
<213> ORGANISM: Glycine max

<400> SEQUENCE: 60
ttcctcaaaa accagc                                                     16

<210> SEQ ID NO 61
<211> LENGTH: 15
<212> TYPE: DNA
<213> ORGANISM: Glycine max

<400> SEQUENCE: 61
tcctcgaaaa ccagc                                                      15

<210> SEQ ID NO 62
<211> LENGTH: 23
<212> TYPE: DNA
<213> ORGANISM: Glycine max

<400> SEQUENCE: 62
tttcataaat caattagagg cta                                             23

<210> SEQ ID NO 63
<211> LENGTH: 19
<212> TYPE: DNA
<213> ORGANISM: Glycine max

<400> SEQUENCE: 63
gaggcttagt tcacttctc                                                  19

<210> SEQ ID NO 64
<211> LENGTH: 16
<212> TYPE: DNA
<213> ORGANISM: Glycine max

<400> SEQUENCE: 64
accatgcatt ctcttg                                                     16

<210> SEQ ID NO 65
<211> LENGTH: 17
<212> TYPE: DNA
<213> ORGANISM: Glycine max

<400> SEQUENCE: 65
accatgcatt cttttga                                                    17

<210> SEQ ID NO 66
<211> LENGTH: 22
<212> TYPE: DNA
<213> ORGANISM: Glycine max

<400> SEQUENCE: 66
tcccttgacg agtctcacac at                                              22

<210> SEQ ID NO 67
<211> LENGTH: 24
<212> TYPE: DNA
<213> ORGANISM: Glycine max

<400> SEQUENCE: 67
ttgcttcttg ttctcctgaa gttg                                            24
```

-continued

<210> SEQ ID NO 68
<211> LENGTH: 18
<212> TYPE: DNA
<213> ORGANISM: Glycine max

<400> SEQUENCE: 68
cagacagaaa cgatgata                                              18

<210> SEQ ID NO 69
<211> LENGTH: 17
<212> TYPE: DNA
<213> ORGANISM: Glycine max

<400> SEQUENCE: 69
cagaaacgat gctattg                                               17

<210> SEQ ID NO 70
<211> LENGTH: 19
<212> TYPE: DNA
<213> ORGANISM: Glycine max

<400> SEQUENCE: 70
gtggcattgg cctttggt                                              19

<210> SEQ ID NO 71
<211> LENGTH: 19
<212> TYPE: DNA
<213> ORGANISM: Glycine max

<400> SEQUENCE: 71
cactgcctct tccctagcc                                             19

<210> SEQ ID NO 72
<211> LENGTH: 18
<212> TYPE: DNA
<213> ORGANISM: Glycine max

<400> SEQUENCE: 72
catgaaacca aacataat                                              18

<210> SEQ ID NO 73
<211> LENGTH: 18
<212> TYPE: DNA
<213> ORGANISM: Glycine max

<400> SEQUENCE: 73
catgaaacca gacataat                                              18

<210> SEQ ID NO 74
<211> LENGTH: 29
<212> TYPE: DNA
<213> ORGANISM: Glycine max

<400> SEQUENCE: 74
gcacgatgaa ttctttgtat gatgtttga                                  29

<210> SEQ ID NO 75
<211> LENGTH: 25
<212> TYPE: DNA
<213> ORGANISM: Glycine max

<400> SEQUENCE: 75
aaagcataac ttgttgtcgc atcaa                                      25

<210> SEQ ID NO 76
<211> LENGTH: 20
<212> TYPE: DNA
<213> ORGANISM: Glycine max

<400> SEQUENCE: 76
ttctgtaata cttgattatc                                              20

<210> SEQ ID NO 77
<211> LENGTH: 20
<212> TYPE: DNA
<213> ORGANISM: Glycine max

<400> SEQUENCE: 77
ttctgtaata catgattatc                                              20

<210> SEQ ID NO 78
<211> LENGTH: 23
<212> TYPE: DNA
<213> ORGANISM: Glycine max

<400> SEQUENCE: 78
tcccttccag gagaattctg aac                                          23

<210> SEQ ID NO 79
<211> LENGTH: 23
<212> TYPE: DNA
<213> ORGANISM: Glycine max

<400> SEQUENCE: 79
tgaaaggcag gactctggtt atg                                          23

<210> SEQ ID NO 80
<211> LENGTH: 17
<212> TYPE: DNA
<213> ORGANISM: Glycine max

<400> SEQUENCE: 80
aaccatcatc cgaatcc                                                 17

<210> SEQ ID NO 81
<211> LENGTH: 16
<212> TYPE: DNA
<213> ORGANISM: Glycine max

<400> SEQUENCE: 81
taaaccatca tccgag                                                  16

<210> SEQ ID NO 82
<211> LENGTH: 459
<212> TYPE: DNA
<213> ORGANISM: Glycine max

<400> SEQUENCE: 82
ttttgatcca aaacaaagct gaaaagaaag gggacaggta tgaagcaatc ttcagcttct    60
actttggaga ctatggtcac atagcagtgc agggaccttc cctgacctat gaggacacat   120
atttggctgt gactggtggg tctggcatat ttgagggtgt taaaggtcaa gtgaagctgc   180
gtcagattgt gtatcctttc aagatttttgt acacatttta tctaaagggt atcaaggatt   240
tgcctcagga gcttcttgtc aagactgttg agccaattcc atctgttgaa ccttcccctg   300

```
ctgctaaggc ccttgagccc aatgctacca ttgctggctt caccgactaa ttcatcaact      360 tttttttgtat ttgctttggc ctttgtagta gtatgattta agttactgaa taataataac     420
aagtggggac tatgatgggt tttgtagtgg tggagtttc                             459
```

<210> SEQ ID NO 83
<211> LENGTH: 1102
<212> TYPE: DNA
<213> ORGANISM: Glycine max

<400> SEQUENCE: 83

```
ttacaccaga atcatggcca ccaatcaaat accccctatca tcttattaca gaaaagggga      60
taagagaagg ggaaaaaaaa tctctagaaa ctgaagaatc aaggtttggt tcaaaaactg      120
tgcagttgcg ttagcatgtg aacaagctca tcactagaag gcctatctgc aggcatatca     180
gagaggcatg cagcagcaat cctaaccgcc attagcatct catcttcctc accttcttcc     240
cctaacatgc tcttatctag agcttcgtgc gcctcgcccg cttgctgcaa gtgtctcagc     300
caacatccca aacttccccc actggctgct ctcccaaaga atggatctgt aggatcctta     360
ccagttaaca aaacacctag tatcatgcca aaactaaaga tgtcactttt gtcagtgtac     420
ctgctgaaat tgccaaaaaa caccattcaa tctgaatacc atgaagctcc acatatacaa     480
gaatggaatg aagttaaaat aaacatctta ttggcaatac catacccata tatgcaatgc     540
catcaatcaa gcaatctttt attgttatta cttattgcta ttgatattga tgcatccaaa     600
tatacaccac tgaaaaacta gaagtattcc aagttaaatt aggaaaaaaa accttttgtca     660 attattatta taatttagtt gtggtctcac tcaccaatct aggtttagta gtttgcagca     720
tgtgaactat aaactatatt attcatttgg accagactta gtgccaactg cctaaggtct     780
aaaacttgac atcaggaagt aatgggtagt tacaaaaaca aatagcaaag tctttattaa     840
ataataccaa attcaatcag caaatgatac aatgacaata cagattacag aatagtaatt     900
tcgtttcaaa acaagagtct ttcattaggg tactacaaag ggggcaaaaa accaatgagg     960
tgtggagctt ttgaaaaggt aacgaatcaa acaaattccc aatatcaacc acctaattac    1020
cctattggtg taaaaaagtg aaagaacaga aacagaccaa gttcaaaaca ctagtgaatg    1080
agtatgattg aaatttgtct ta                                             1102
```

<210> SEQ ID NO 84
<211> LENGTH: 402
<212> TYPE: DNA
<213> ORGANISM: Glycine max

<400> SEQUENCE: 84

```
tcagttacgc aagttttgaa gctgttggtt atgactttaa tgacatggct ctaggtgaac      60
ttgtggaaag gattttagct tgcttttgtc cagcagagtt ttctgttgct ttgcacattg     120
acatgcatgg tgagaaactt aataaatttc ccttagacat caaaggatac tactgtggtg     180
agaggagcac tgaagagctt ggagtaggtg gtgcagttgt gtaccaaaca tttgttcaag     240
gctgcgatgg tagtgcatct cctaggtcta ttctgaaatg ctgctggagt gaggacgaga     300
acgaagatga agtgagggag atataagtac ttctggtttt tatgttctgt tgttatttat     360
ctttactgtc gagtgtgtta ttacctaaat aaataaatat gg                        402
```

<210> SEQ ID NO 85
<211> LENGTH: 466
<212> TYPE: DNA
<213> ORGANISM: Glycine max

<400> SEQUENCE: 85

```
atcctcaaat acaagtccct gatctcatca tacctaagtt gttaaagaaa atctagccca      60
ttccatataa atcttattaa taccttactc caggacctga agacaacct acccaactat     120
cattaaacaa tttagtctat accacctatg cccaaataga tatagatata tagaaacaaa     180
ccaggtggaa gaggaataac agagaagtgt ataaaataaa tatgcaactt cagacttgta     240
tgctcaagcc gcaagcttat atttgaagat gtctatccca caattccaga tccacctaaa     300
caagaataaa aatccacaaa acattagaag cgaattcgct gctgcaaatt agaatataaa     360
attcttaaaa ataatcctta ccaaaagatt catcacatta ataatagtat ccatgcccat     420
gtgagccatc accccgtaa taagatgaat atgaacctct accata                    466
```

<210> SEQ ID NO 86
<211> LENGTH: 489
<212> TYPE: DNA
<213> ORGANISM: Glycine max

<400> SEQUENCE: 86

```
atctcaatct gctttgacag atagagagaa ggagaatctt gacaacttag ttgacaagga      60
gtgtgcaacc acagagggta tgatatcgag ccagctcaag ttgaagtctt ctttgtcatc     120
caaagcgtct tctcatcaaa gcatggacaa acatgcaatc cttcgacgta tcaggcaacg     180
caggtttaat aacaaagcca aaccgctct ggaagctctc ataggcacct cagaagccaa     240
caataccggc actgcccaag aacagaagtg gcttcaactg ggtgactctt tctcatctcc     300
ttaactggaa acacaatctc cccccagttt gcaacccatc tataaatacc ctctttagtt     360
tccttcaccc aacaaagtca tcttttccat acgcttgcat ggctaggaaa ggaaatccaa     420
cccgatcttt atcggcatgc ttaagaaatc ccactatgta tctattaact gtagtagacc     480
ttgtcggtt                                                            489
```

<210> SEQ ID NO 87
<211> LENGTH: 794
<212> TYPE: DNA
<213> ORGANISM: Glycine max

<400> SEQUENCE: 87

```
ccaaccacgc tgattcttta ggccatcagt caacaaatta ctctggaaac tgctaaggaa      60
tataaacctt gaaccagaca tgtcccctga agagtagaaa aatatcatgt ttcagcagca     120
tggttcaaga aaatttgttc atgtaggcaa aattgatttt gaaagaaatt gattatgcaa     180
aattaatgtt ggttaagatt aattttaaag taatgtgatt tatgtttgaa tatttttat     240
cgtagcaact cagtataact tttttaattc aatgcaaaaa tattcaaagt tattttgact     300
caatcaattc tagattcaat atcaattcct catcattgaa acaaatgcca acatgtattt     360
aaaatcacga tagttgatat ttcaacgtaa ttcaagaaaa ttcaacataa aactaaacac     420
gcatcactta atgcgtgcta gggtgagcat taaaattgat ttcaaataaa attaattttc     480
taaaattggt tttggtaaaa attgattttg aagtgacatg agttatgttt gaacgttttt     540
tattctaaaa gttaataaca aatttcaatt ttttttatc caaagcaaaa gtcatctaaa     600
agttatttga actcgaaatc aaatttaaac tcaaaatcaa ttccttaatg tgaaattaaa     660
catgtgtcca tttacctcaa atcatgttat ccgatatttc aacaagactt taagaatcc     720
tacgtgaaac caaacatgca cttactagaa taagcagagt gaatagcaga aatacccaga     780
```
ttgtaagctg caga                                                         794

<210> SEQ ID NO 88
<211> LENGTH: 568
<212> TYPE: DNA
<213> ORGANISM: Glycine max

<400> SEQUENCE: 88
atgaatagag acaaatccac agaaacaaat aaacagcaca aaagctacaa aagtaaagtc        60
ttgaggtaaa aaattggcac tagcagaaac aaaatatagt gaaggaacca gatcatgata       120
aatgctaata aagtgggaaa aaaatcggtt gaataattaa acaaaattaa ttacaaagct       180
aagtatataa ttcaactgtt agaagaaaaa aagtcgttat gcattcctaa aaggcaaggc       240
acagtcaacc taaataattt ccctaaatat tttccctca acccactaca atattttaaa        300
atagccatga aaatagatta ctagatcaaa attacaaaag taattaatat acaatatcat       360
tggtttaaca aattacacca cagaagaaaa ataccatcca caaccaagag aagatgacat       420
aagatattga tatcaaagaa aagtctaggc atataataaa accattaaat cagtacaaac       480
tacactcaga aataaatagc catcttactg ccaggctaat ataaaaaatg gtcactgaag       540
tttatgactt tgtgcaactg tgtaaaac                                          568

<210> SEQ ID NO 89
<211> LENGTH: 503
<212> TYPE: DNA
<213> ORGANISM: Glycine max

<400> SEQUENCE: 89
ccgagacgag tgaggaaatc ctcgaggtgg gtcaaggacc cctcgtgctt gcttgggtcg        60
aacatggagg caacgagagt acaaaatgtt agggacacaa taagctggtt ttcgaggaac       120
tagtacctcc agcaattcaa taaagaagaa gaagaacaaa gagggaaaga gtgaggtaat       180
tggaaatttc attcatgcct tgcttgttat ttacattagt attttataaac ttcctagtaa      240
cagaaagatc ctaggaatat ttgcccataa caaaatttgt acacattgtc ccctaggagc       300
agacaatatc aaccaaggaa attctagaag gtagcctcag ctggtctcac ccttcttcca       360
aaaacgtact ctttgaggta agaaggtttt gtaattcttc tttcgaactt agcttcttcc       420
tgtaccccct catttgcttt tgtgaccccc gcccttgcct ctgtttgtaa gctcgtatca       480
acatgtttcc gatacagatg cag                                               503

<210> SEQ ID NO 90
<211> LENGTH: 762
<212> TYPE: DNA
<213> ORGANISM: Glycine max

<400> SEQUENCE: 90
aacagagttg gctataacaa ggttttggat aatgccaagc ccatgaatga tccagatgga        60
aggcactttt catcttttac ttacctgagg cttagttcac ttctcatgga acgacaaaac       120
ttcatagagt ttgaaagatt tgtcaagaga atgcatggta agttgatgaa gaaaatttta       180
aatgtatctc tagcctctaa ttgatttatg aaaatatcta ttaaggaaag aaaatcatcc       240
ctttatctgg ccttgattga atgaatgctc acgtgtcatc tgaaaccttc ttactccaca       300
gtcccacact cagtagggta atcagcaaaa ccctgaagac ccaaatttct ttcagaggca       360
tggttcagca actgtactaa tatcatattg aactttggat tccattattc gctcccactg       420
atagtgttct ttgatccacc tagcactagt cttttttatct gattggaatc attttataaa      480

```
taattgaaca cgaaaggagt attaatgtca gttttaagag gtgtacttct cttggagaga    540
aaaacactga aactttaagt agctgcaaaa gttgttgcta tcttgtggga cattgattat    600
attagggttg atgactgtgt catttctcat tgcagggaa gctgttcttg atcttcaggt     660
ataaccggtg ggaaacaaag tcttgttgaa tttgtattta taagtcccct gacaaaatgg    720
ttgggggtat tctgttatag aataggagaa ataggattgt ta                      762

<210> SEQ ID NO 91
<211> LENGTH: 513
<212> TYPE: DNA
<213> ORGANISM: Glycine max

<400> SEQUENCE: 91
gagaaagaga agtattgcgc atcatgccca aatgtggcca cacttttcat ctttcttgca     60
ttgatatatg gctgaggaaa caatccacct gtccagtatg ccgtctgccg ttgaaaaact    120
cttccgaaac gaaacatgtg agacctgtga catttaccat gagccaatcc cttgacgagt    180
ctcacacatc agacagaaac gatgatattg agagatatgt tgaacctaca cctactgcag    240
ccagtaactc tttacaacca acttcaggag aacaagaagc aaggcaatga tcttagagaa    300
ctaaaggggt tgttctgctc aaaaagagaa gaatgtagaa tttctgcttc tatagaggaa    360
tgcttctaat tatagattgg attcaaattc tttgtctgta atatggcctt catattcact    420
tggtggtgta aatatgtttc cttttgtagc atatgcgggc caaggttttg gtggaatttc    480
ttgcataccg atttgaagtt cttttgtcta tgg                                513

<210> SEQ ID NO 92
<211> LENGTH: 280
<212> TYPE: DNA
<213> ORGANISM: Glycine max

<400> SEQUENCE: 92
atccaccaac accacttcac caccaaagcc tagtggagct gtaactgttt ccagtggcat     60
tggccttttg gtggggtctt tctttgtgtc agcaattatg tttggtttca tgggctaggg    120
aagaggcagt gctgtttttt ttttattctc ctttttatta atatgttatt gttttgctga    180
gagtttgtgt gaatttcatc atttaatcca gatgtatatc taatcttgat atgtatctcc    240
ttttaatatt taaaaatgac acatttcttt agctgcttcc                         280

<210> SEQ ID NO 93
<211> LENGTH: 883
<212> TYPE: DNA
<213> ORGANISM: Glycine max

<400> SEQUENCE: 93
agatttcgtt tctgggtatc agaaaacacc taggttccga ttagatttct atattttgcc     60
tagacgtcaa atgcacgatg aattctttgt atgatgtttg aaaattgaag tcttctgtaa    120
tacttgatta tcaacctcaa attttgatgc gacaacaagt tatgctttgt gaagttgtta    180
ttgatgattg tatggtgtga tttggtttca ggtttgaaac ttgttactgt ggaccgtcct    240
tttgctgaga agcactatgc tgatttgtct gccaagcctt tctttagtgg tttggtggat    300
tacattatct ctggccctgt tgttgccatg atctgggagg gcaagaatgt tgttacaact    360
ggccgaaaga ttatcggagc cacaaaccca gctcaatctg agcctggaac tatccgtggt    420
gactttgcca ttgacattgg aaggtataga cttgttttca tcatcgttca agcaagttta    480
```

-continued

```
cgttttcaaa tcttttgttt taacacatga atatgaatct gttttcattg ttgttcatgt    540
ttctaatcta gtttggtgga tgttaggttt tcatttttgt tgtttgattt tcaatttctc    600
ccgaattttt ttcttattta caacattggt ttccaacgtt ctgtgtttta gagaaaagag    660
tgttgtgctc aaccaattct gcgaatattg caatatgttc atgacatcat caattaagca    720
agatgataac actgttgagt acatcataat caaggcagtg gaatccaaac aaatccatgt    780
tctgtatctt tgtattcatg aaaatcaaaa attgttgttt tagtcaatgt ttatcaacat    840
tgctcttagt gtggatctag atacttatta tttacaattc tat                      883

<210> SEQ ID NO 94
<211> LENGTH: 475
<212> TYPE: DNA
<213> ORGANISM: Glycine max

<400> SEQUENCE: 94
atgaccaacc taccgcctgt gggtaaagct aaactaagtt ctcacaggtg aggtgagttc     60
accaaccacg gccgccagaa tttccagatc cccatccgtt ccctgatgct gctttcttgg    120
gggcagatcc ccagccagag cttccttgtt caccatcact tggaccagca ccaccactcg    180
cttgtccccc ccagccacca ttgtcactgt tactagctcc acctcctccc cctccccaac    240
cactactgcc tccaccgctt ccaccaccac caccccaacc accaggaaaa gcttcccttc    300
caggagaatt ctgaaccttg gcccctggaa aattgcttaa accatcatcc gagtcctttg    360
tattattaga accccatctg cccccataac cagagtcctg cctttcatta ttggagttgt    420
ctcctctatt gttataagaa cctcgaccac gaccacgtcc acgccctctt ccacc         475
```

MARKERS ASSOCIATED WITH SOYBEAN RUST RESISTANCE AND METHODS OF USE THEREFOR

CROSS REFERENCE TO RELATED APPLICATIONS

The following application is a divisional application of U.S. patent application Ser. No. 12/690,782 filed on Jan. 20, 2010, which itself claims the benefit of International Patent Application No. PCT/US2009/051003 filed on Jul. 17, 2009 which claims the benefit of U.S. Provisional Patent Application Ser. Nos. 61/081,989 and 61/153,495, filed Jul. 18, 2008 and Feb. 18, 2009, respectively. The disclosure of each of which is incorporated herein by reference in its entirety.

STATEMENT REGARDING ELECTRONIC FILING OF A SEQUENCE LISTING

A Sequence Listing in ASCII text format, submitted under 37 C.F.R. § 1.821, entitled "72001-US-REG-D-NAT-1_SeqList_DIV_US_ST25", 34.2 kilobytes in size, generated on Sep. 1, 2015 and filed via EFS-Web, is provided in lieu of a paper copy. This Sequence Listing is hereby incorporated by reference into the specification for its disclosures.

TECHNICAL FIELD

The presently disclosed subject matter relates to markers associated with soybean rust (SBR) resistance and methods of use therefor. More particularly, the presently disclosed subject matter relates to screening soybean lines for resistance to SBR and for producing soybean lines with improved resistance to SBR, the methods involving genetic marker analysis.

BACKGROUND

Plant pathogens are known to cause massive damage to important crops, resulting in significant agricultural losses with widespread consequences for both the food supply and other industries that rely on plant materials. As such, there is a long felt need to reduce the incidence and/or impact of agricultural pests on crop production.

Soybean rust (SBR), which is caused by the obligate fungal pathogen *Phakopsora pachyrhizi* H. Sydow & Sydow, was first reported in Japan in 1902. By 1934, the pathogen was reported in several other Asian countries and in Australia. More recently, *P. pachyrhizi* infection has been reported in Africa, and has spread rapidly through the African continent.

In November 2004, *P. pachyrhizi* was first reported in the continental U.S., and the pathogen has now been reported in more than 300 U.S. counties, in Canada, and in Mexico. In 2007, approximately 0.5 million hectares of soybean were sprayed for SBR control in the U.S.

SBR has the potential to cause significant yield losses in the U.S., as indicated by fungicide trials in Georgia and Florida that reported yield losses of 30 to 33% in untreated control plots. In Brazil, the total yield loss in the 2006-2007 growing season due to SBR was estimated to be over U.S. $2.26 billion with an average of 2.3 fungicide applications required per season. Yield losses up to 80% have been reported due to severe outbreaks of SBR, which result in early leaf drop that inhibits pod set. Consistent economic losses in Brazil over the last several years due to severe SBR outbreaks have raised concerns regarding the potential impact of this disease in the United States.

Soybean cultivars currently available commercially in the United States are all susceptible to SBR to some degree, and fungicide applications are currently employed to control the disease.

Therefore, soybean rust resistant cultivars are needed to reduce fungicide costs and yield losses due to SBR.

SUMMARY

The presently disclosed subject matter provides methods for conveying resistance to soybean rust (SBR) into non-resistant soybean germplasm. In some embodiments, the methods comprise introgressing SBR resistance into a non-resistant soybean using one or more nucleic acid markers for marker-assisted breeding among soybean lines to be used in a soybean breeding program, wherein the markers are linked to an SBR resistance locus selected from the group consisting of Rpp1, Rpp2, Rpp3, Rpp4, and Rpp5.

The presently disclosed subject matter also provides methods for reliably and predictably introgressing soybean rust (SBR) resistance into non-resistant soybean germplasm. In some embodiments, the methods comprise employing one or more nucleic acid markers for marker-assisted breeding among soybean lines to be used in a soybean breeding program.

The presently disclosed subject matter also provides methods for producing a soybean plant adapted for conferring resistance to soybean rust (SBR). In some embodiments, the methods comprise (a) selecting a first donor parental line possessing a desired SBR resistance and having at least one of the resistant loci selected from a locus mapping to Rpp1 and mapped by one or more of the markers SEQ ID NOs: 1-3; a locus mapping to Rpp2 and mapped by one or more of the markers SEQ ID NOs: 4-6; a locus mapping to Rpp3 and mapped by one or more of the markers SEQ ID NOs: 7 and 8; a locus mapping to Rpp4 and mapped by one or more of the markers SEQ ID NOs: 9 and 10; and a locus mapping to Rpp5 and mapped one or more markers SEQ ID NOs: 11-13; (b) crossing the first donor parent line with a second parental line in hybrid combination to produce a segregating plant population; (c) screening the segregating plant population for identified chromosomal loci of one or more genes associated with the resistance to SBR; and (d) selecting plants from the population having the identified chromosomal loci for further screening until a line is obtained which is homozygous for resistance to SBR at sufficient loci to give resistance to SBR.

The presently disclosed subject matter also provides methods for selecting a soybean rust (SBR) resistant soybean plant. In some embodiments, the methods comprise (a) genotyping one or more soybean plants with respect to one or more single nucleotide polymorphisms (SNPs); and (b) selecting a soybean plant that includes at least one resistance allele associated with the SNPs, thereby selecting an SBR resistant soybean plant.

In some embodiments, the presently disclosed methods comprise (a) isolating one or more nucleic acids from a plurality of soybean plants; (b) detecting in said isolated nucleic acids the presence of one or more marker molecules associated with SBR resistance, wherein said marker molecule is selected from the group consisting of SEQ ID NOs: 1-13; and (c) selecting a soybean plant comprising said one or more marker molecules, thereby selecting an SBR resistant soybean plant.

In some embodiments, the one or more nucleic acid markers are selected from the group consisting of SEQ ID NOs: 1-13, and informative fragments thereof. In some embodiments, the methods and compositions of the presently disclosed subject matter employ a marker molecule mapped within 1, 2, 3, 4, 5, 6, 7, 8, 9, or 10 centiMorgans or less from a marker molecule selected from the group consisting of SEQ ID NOs: 1-13.

In some embodiments, the marker-assisted breeding comprises single nucleotide polymorphism (SNP) analysis. In some embodiments, the methods further comprise screening an introgressed soybean plant, or a cell or tissue thereof, for SBR resistance In some embodiments of the presently disclosed methods, the at least one resistance allele is associated with an allele having an A at nucleotide 428 of SEQ ID NO: 1; a T at position 895 of SEQ ID NO: 2; a G at position 932 of SEQ ID NO: 2; a T at position 57 of SEQ ID NO: 3; a G at position 213 of SEQ ID NO: 4; a G at position 441 of SEQ ID NO: 4; an A at position 70 of SEQ ID NO: 5; a T at position 348 of SEQ ID NO: 5; an A at position 715 of SEQ ID NO: 6; a C at position 377 of SEQ ID NO: 7; a T at position 100 of SEQ ID NO: 8; a G at position 113 of SEQ ID NO: 8; a T at position 147 of SEQ ID NO: 9; a C at position 205 of SEQ ID NO: 10; an A at position 102 at SEQ ID NO: 11; A T at position 159 of SEQ ID NO: 12; and/or a G at position 357 of SEQ ID NO: 13.

The presently disclosed subject matter also provides soybean rust (SBR) resistant soybean plants, parts thereof (including but not limited to pollen, ovule, leaf, embryo, root, root tip, anther, flower, fruit, stem, shoot, seed; rootstock, protoplast, and callus), and progeny thereof, selected using the disclosed methods.

Thus, it is an object of the presently disclosed subject matter to provide methods for conveying SBR resistance into non-resistant soybean germplasm, which object is achieved in whole or in part by the presently disclosed subject matter.

BRIEF DESCRIPTION OF THE SEQUENCE LISTING

Figure 1A:
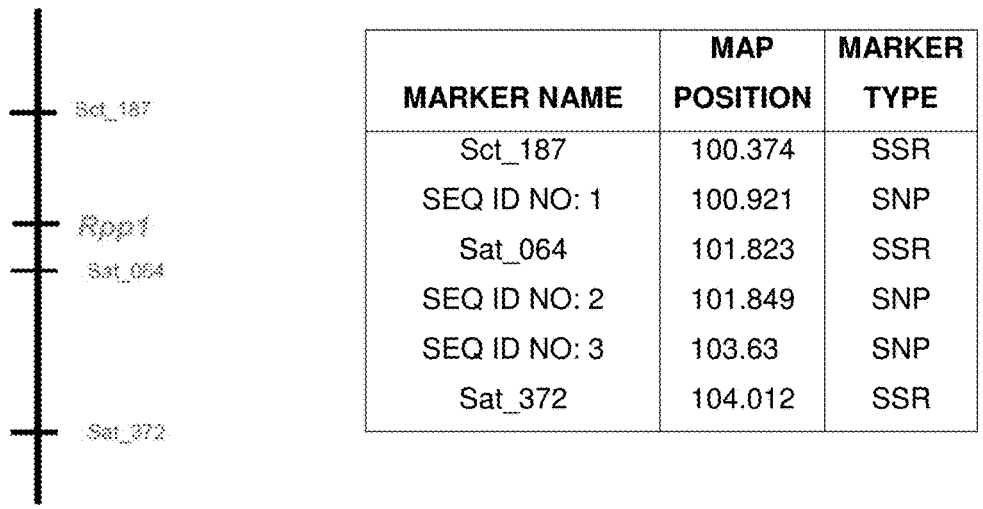
FIGS. 1A-1E are genetic linkage maps depicting linkage groups and showing relative positions of various markers linked to Rpp1-Rpp5, respectively.

SEQ ID NOs: 1-13 are nucleotide sequences of the soybean genome comprising single nucleotide polymorphisms (SNPs) identified as being associated with the Rpp1 gene, the Rpp2 gene, the Rpp3 gene, the Rpp4 gene, and/or the Rpp5 gene as set forth in Table 1.

SEQ ID NOs: 14-81 are nucleotide sequences of oligonucleotide primers that can be employed to amplify and/or otherwise assay a subsequence of the soybean genome that is associated with the Rpp1-Rpp5 loci as also set forth in Table 1.

TABLE 1

Amplification and Detection Primers

| Rpp Gene | Genomic Subsequence SEQ ID NO: | Amplification Primer SEQ ID NOs. | Detection Primers SEQ ID NOs. |
|---|---|---|---|
| 1 | 1 | 14 and 15 | 16 and 17 |
| 1 | 2 | 18 and 19 | 20 and 21 |
| 1 | 2 | 22 and 23 | 24 and 25 |
| 1 | 3 | 26 and 27 | 28 and 29 |
| 2 | 4 | 30 and 31 | 32 and 33 |
| 2 | 4 | 34 and 35 | 36 and 37 |
| 2 | 5 | 38 and 39 | 40 and 41 |
| 2 | 5 | 42 and 43 | 44 and 45 |
| 2 | 6 | 46 and 47 | 48 and 49 |
| 3 | 7 | 50 and 51 | 53 and 53 |
| 3 | 8 | 54 and 55 | 56 and 57 |
| 3 | 8 | 58 and 59 | 60 and 61 |
| 4 | 9 | 62 and 63 | 64 and 65 |
| 4 | 10 | 66 and 67 | 68 and 69 |
| 5 | 11 | 70 and 71 | 72 and 73 |
| 5 | 12 | 74 and 75 | 76 and 77 |
| 5 | 13 | 78 and 79 | 80 and 81 |

SEQ ID NOs: 82-94 corresponds to subsequences of the preliminary assembly of the soybean (*Glycine max*) genomic sequence present in the Phytozyme Database, which correspond to SEQ ID NOs: 1-13 as set forth in Table 2.

TABLE 2

Locations of SEQ ID NOs: 1-13 in the Phytozyme Database

| SEQ ID NO: | Relevant Nucleotides | Nucleotide Positions in Phytozyme Database | Percent Identity |
|---|---|---|---|
| 1 | 1-459 | 60469363-60469821 | 99.8 |
| 2 | 1-1101 | 60577757-60578858 | 99.1 |
| 3 | 23-424 | 60291869-60292270 | 98.8 |
| 4 | 1-470 | 27963429-27963894 | 99.6 |
| 5 | 1-489 | 30065112-30065600 | 99.4 |
| 6 | 1-794 | 30330727-30331520 | 98.7 |
| 7 | 1-568 | 46665732-46666299 | 99.3 |
| 8 | 1-503 | 41676695-41677197 | 98.8 |
| 9 | 1-769 | 56338383-56339144 | 97.9 |
| 10 | 1-513 | 55961511-55962023 | 99.6 |
| 11 | 1-281 | 33395967-33396246 | 99.3 |
| 12 | 36-916 | 33200392-33201274 | 97.4 |
| 13 | 5-479 | 35318068-35318542 | 99.4 |

DETAILED DESCRIPTION

The presently disclosed subject matter relates at least in part to the identification of several SNPs associated with SBR resistance in *Glycine* sp. Thus, provided herein are methods of conveying SBR resistance into non-resistant soybean germplasm, which employ one or more of the identified SNPs in various approaches.

All references listed below, as well as all references cited in the instant disclosure, including but not limited to all patents, patent applications and publications thereof, scientific journal articles, and database entries (e.g., GEN-BANK® database entries and all annotations available therein) are incorporated herein by reference in their entireties to the extent that they supplement, explain, provide a background for, or teach methodology, techniques, and/or compositions employed herein.

I. Definitions

Unless defined otherwise, all technical and scientific terms used herein have the same meaning as commonly understood to one of ordinary skill in the art to which the presently disclosed subject matter belongs.

Following long-standing patent law convention, the articles "a", "an", and "the" refer to "one or more" when used in this application, including in the claims. For example, the phrase "a marker" refers to one or more markers. Similarly, the phrase "at least one", when employed herein to refer to an entity, refers to, for example, 1, 2, 3, 4, 5, 6, 7, 8, 9, 10, 15, 20, 25, 30, 35, 40, 45, 50, 75, 100, or more of that entity, including but not limited to whole number values between 1 and 100 and greater than 100.

Unless otherwise indicated, all numbers expressing quantities of ingredients, reaction conditions, and so forth used in the specification and claims are to be understood as being modified in all instances by the term "about". Accordingly, unless indicated to the contrary, the numerical parameters set forth in this specification and attached claims are approximations that can vary depending upon the desired properties sought to be obtained by the presently disclosed subject matter.

As used herein, the term "about," when referring to a value or to an amount of mass, weight, time, volume, concentration or percentage is meant to encompass variations of in some embodiments ±20%, in some embodiments ±10%, in some embodiments ±5%, in some embodiments ±1%, in some embodiments ±0.5%, and in some embodiments ±0.1% from the specified amount, as such variations are appropriate to perform the disclosed method.

As used herein, the term "allele" refers to any of one or more alternative forms of a gene, all of which relate to at least one trait or characteristic. In a diploid cell, two alleles of a given gene occupy corresponding loci on a pair of homologous chromosomes, although one of ordinary skill in the art understands that the alleles in any particular individual do not necessarily represent all of the alleles that are present in the species. Since the presently disclosed subject matter relates to SNPs, it is in some instances more accurate to refer to a "haplotype" (i.e., an allele of a chromosomal segment) instead of "allele". However, in such instances, the term "allele" should be understood to comprise the term "haplotype".

As used herein, the phrase "associated with" refers to a recognizable and/or assayable relationship between two entities. For example, a trait, locus, QTL, SNP, gene, marker, phenotype, etc. is "associated with resistance" if the presence or absence of the trait, locus, QTL, SNP, gene, marker, phenotype, etc., influences an extent or degree of resistance (e.g., resistance to SBR). In some embodiments, an allele associated with resistance to SBR comprises an allele having an A at nucleotide 428 of SEQ ID NO: 1; a T at position 895 of SEQ ID NO: 2; a G at position 932 of SEQ ID NO: 2; a T at position 57 of SEQ ID NO: 3; a G at position 213 of SEQ ID NO: 4; a G at position 441 of SEQ ID NO: 4; an A at position 70 of SEQ ID NO: 5; a T at position 348 of SEQ ID NO: 5; an A at position 715 of SEQ ID NO: 6; a C at position 377 of SEQ ID NO: 7; a T at position 100 of SEQ ID NO: 8; a G at position 113 of SEQ ID NO: 8; a T at position 147 of SEQ ID NO: 9; a Cat position 205 of SEQ ID NO: 10; an A at position 102 at SEQ ID NO: 11; A T at position 159 of SEQ ID NO: 12; and/or a G at position 357 of SEQ ID NO: 13.

As used herein, the term "backcross", and grammatical variants thereof, refers to a process in which a breeder crosses a progeny individual back to one of its parents, for example, a first generation hybrid F1 with one of the parental genotypes of the F1 hybrid. In some embodiments, a backcross is performed repeatedly, with a progeny individual of one backcross being itself backcrossed to the same parental genotype.

The term "chromosome" is used herein in its art-recognized meaning of the self-replicating genetic structure in the cellular nucleus containing the cellular DNA and bearing in its nucleotide sequence the linear array of genes.

As used herein, the terms "cultivar" and "variety" refer to a group of similar plants that by structural or genetic features and/or performance can be distinguished from other varieties within the same species.

As used herein, the term "gene" refers to a hereditary unit including a sequence of DNA that occupies a specific location on a chromosome and that contains the genetic instruction for a particular characteristics or trait in an organism.

As used herein, the term "hybrid" in the context of plant breeding refers to a plant that is the offspring of genetically dissimilar parents produced by crossing plants of different lines or breeds or species, including but not limited to the cross between two inbred lines.

As used herein, the term "inbred" refers to a substantially homozygous individual or line.

As used herein, the phrase "informative fragment" refers to a nucleic acid molecule and/or its nucleotide sequence that allows for the proper identification of which allele of an allele set (e.g., an SNP) the nucleic acid molecule and/or the nucleotide sequence corresponds to. For example, whereas the SNP that corresponds to SEQ ID NO: 1 relates to an "A" or a "G" at position 428, an "informative fragment" of SEQ ID NO: 1 would be any sequence that comprises position 428 of SEQ ID NO: 1, thereby allowing the nucleotide that is present in that position to be determined.

As used herein, the terms "introgression", "introgressed", and "introgressing" refer to both a natural and artificial process whereby genomic regions of one species, variety, or cultivar are moved into the genome of another species, variety, or cultivar, by crossing those species. The process can optionally be completed by backcrossing to the recurrent parent.

As used herein, the term "linkage" refers to a phenomenon wherein alleles on the same chromosome tend to be transmitted together more often than expected by chance if their transmission was independent. Thus, in some embodiments two alleles on the same chromosome are said to be "linked" when they segregate from each other in the next generation less than 50% of the time, less than 25% of the time, less than 20% of the time, less than 15% of the time, less than 10% of the time, less than 5% of the time, less than 4% of the time, less than 3% of the time, less than 2% of the time, or less than 1% of the time. Thus, two loci are linked if they are within 50, 25, 20, 15, 10, 5, 4, 3, 2, or 1 centiMorgans (cM) of each other. For example, in some embodiments an SNP is linked to a marker if it is within 50, 25, 20, 15, 10, 9, 8, 7, 6, 5, 4, 3, 2, or 1 cM of the marker.

As used herein, the phrase "linkage group" refers to all of the genes or genetic traits that are located on the same chromosome. Within the linkage group, those loci that are close enough together can exhibit linkage in genetic crosses. Since the probability of crossover increases with the physical distance between loci on a chromosome, loci for which the locations are far removed from each other within a linkage group might not exhibit any detectable linkage in direct genetic tests. The term "linkage group" is mostly used to refer to genetic loci that exhibit linked behavior in genetic systems where chromosomal assignments have not yet been made. Thus, the term "linkage group" is synonymous with the physical entity of a chromosome, although one of ordinary skill in the art will understand that a linkage group can also be defined as corresponding to a region of (i.e., less than the entirety) of a given chromosome.

As used herein, the term "locus" refers to a position that a given gene or a regulatory sequence occupies on a chromosome of a given species.

As used herein, the term "marker" refers to an identifiable position on a chromosome the inheritance of which can be monitored. In some embodiments, a marker comprises a known or detectable nucleic acid sequence.

In some embodiments, a marker corresponds to an amplification product generated by amplifying a *Glycine* sp. nucleic acid with two oligonucleotide primers, for example, by the polymerase chain reaction (PCR). As used herein, the phrase "corresponds to an amplification product" in the context of a marker refers to a marker that has a nucleotide sequence that is the same (allowing for mutations introduced by the amplification reaction itself) as an amplification product that is generated by amplifying *Glycine* sp. genomic DNA with a particular set of primers. In some embodiments, the amplifying is by PCR, and the primers are PCR primers that are designed to hybridize to opposite strands of the *Glycine* sp. genomic DNA in order to amplify a *Glycine* sp. genomic DNA sequence present between the sequences to which the PCR primers hybridize in the *Glycine* sp. genomic DNA. In some embodiments, a marker that "corresponds to" an amplified fragment is a marker that has the same sequence of one of the strands of the amplified fragment.

As used herein, the term "soybean" refers to a plant, or a part thereof, of the genus *Glycine* including, but not limited to *Glycine max*.

As used herein, the phrase "soybean-specific DNA sequence" refers to a polynucleotide sequence having a nucleotide sequence homology of in some embodiments more than 50%, in some embodiments more than 60%, in some embodiments more than 70%, in some embodiments more than 80%, in some embodiments more than 85%, in some embodiments more than 90%, in some embodiments more than 92%, in some embodiments more than 95%, in some embodiments more than 96%, in some embodiments more than 97%, in some embodiments more than 98%, and in some embodiments more than 99% with a sequence of the genome of the species *Glycine* that shows the greatest similarity to it. In the case of markers for any of the Rpp genes, a "soybean-specific DNA sequence" can comprise a part of the DNA sequence of a soybean genome that flanks and/or is a part of an Rpp gene sequence.

As used herein, the phrase "molecular marker" refers to an indicator that is used in methods for visualizing differences in characteristics of nucleic acid sequences. Examples of such indicators are restriction fragment length polymorphism (RFLP) markers, amplified fragment length polymorphism (AFLP) markers, single nucleotide polymorphisms (SNPs), insertion and deletion mutations (INDEL), microsatellite markers (SSRs), sequence-characterized amplified regions (SCARs), cleaved amplified polymorphic sequence (CAPS) markers or isozyme markers or combinations of the markers described herein which defines a specific genetic and chromosomal location. A molecular marker "linked to" or "associated with" an Rpp gene as defined herein can thus refer to SNPs, insertion mutations, as well as more usual AFLP markers or any other type of marker used in the field.

As used herein, the phrase "nucleotide sequence homology" refers to the presence of homology between two polynucleotides. Polynucleotides have "homologous" sequences if the sequence of nucleotides in the two sequences is the same when aligned for maximum correspondence. The "percentage of sequence homology" for polynucleotides, such as 50, 60, 70, 80, 90, 95, 98, 99 or 100 percent sequence homology, can be determined by comparing two optimally aligned sequences over a comparison window (e.g., about 20-200 contiguous nucleotides), wherein the portion of the polynucleotide sequence in the comparison window can include additions or deletions (i.e., gaps) as compared to a reference sequence for optimal alignment of the two sequences. Optimal alignment of sequences for comparison can be conducted by computerized implementations of known algorithms, or by visual inspection. Readily available sequence comparison and multiple sequence alignment algorithms are, respectively, the Basic Local Alignment Search Tool (BLAST®; Altschul et al. (1990) *J Mol Biol* 215:403-10; Altschul et al. (1997) *Nucleic Acids Res* 25:3389-3402) and ClustalX (Chenna et al. (2003) *Nucleic Acids Res* 31:3497-3500) programs, both available on the Internet. Other suitable programs include, but are not limited to, GAP, BestFit, PlotSimilarity, and FASTA, which are part of the Accelrys GCG Package available from Accelrys Software, Inc. of San Diego, Calif., United States of America.

As used herein, the term "offspring" plant refers to any plant resulting as progeny from a vegetative or sexual reproduction from one or more parent plants or descendants thereof. For instance, an offspring plant can be obtained by cloning or selfing of a parent plant or by crossing two parent plants and include selfings as well as the F1 or F2 or still further generations. An F1 is a first-generation offspring produced from parents at least one of which is used for the first time as donor of a trait, while offspring of second generation (F2) or subsequent generations (F3, F4, and the like) are specimens produced from selfings or crossings of F1s, F2s and the like. An F1 can thus be (and in some embodiments is) a hybrid resulting from a cross between two true breeding parents (the phrase "true-breeding" refers to an individual that is homozygous for one or more traits), while an F2 can be (and in some embodiments is) an offspring resulting from self-pollination of the F1 hybrids.

As used herein, the term "phenotype" refers to a detectable characteristic of a cell or organism, which characteristics are at least partially a manifestation of gene expression.

As used herein, the phrase "plant part" refers to a part of a plant, including single cells and cell tissues such as plant cells that are intact in plants, cell clumps, and tissue cultures from which plants can be regenerated. Examples of plant parts include, but are not limited to, single cells and tissues from pollen, ovules, leaves, embryos, roots, root tips, anthers, flowers, fruits, stems, shoots, and seeds; as well as scions, rootstocks, protoplasts, calli, and the like.

As used herein, the term "population" refers to a genetically heterogeneous collection of plants sharing a common genetic derivation.

As used herein, the term "primer" refers to an oligonucleotide which is capable of annealing to a nucleic acid target and serving as a point of initiation of DNA synthesis when placed under conditions in which synthesis of a primer extension product is induced (e.g., in the presence of nucleotides and an agent for polymerization such as DNA polymerase and at a suitable temperature and pH). A primer (in some embodiments an extension primer and in some embodiments an amplification primer) is in some embodiments single stranded for maximum efficiency in extension and/or amplification. In some embodiments, the primer is an oligodeoxyribonucleotide. A primer is typically sufficiently long to prime the synthesis of extension and/or amplification products in the presence of the agent for polymerization. The minimum lengths of the primers can depend on many factors, including, but not limited to temperature and composition (A/T vs. G/C content) of the primer.

In the context of amplification primers, these are typically provided as a pair of bi-directional primers consisting of one forward and one reverse primer or provided as a pair of forward primers as commonly used in the art of DNA amplification such as in PCR amplification.

As such, it will be understood that the term "primer", as used herein, can refer to more than one primer, particularly in the case where there is some ambiguity in the information regarding the terminal sequence(s) of the target region to be amplified. Hence, a "primer" can include a collection of primer oligonucleotides containing sequences representing the possible variations in the sequence or includes nucleotides which allow a typical base pairing.

Primers can be prepared by any suitable method. Methods for preparing oligonucleotides of specific sequence are known in the art, and include, for example, cloning and restriction of appropriate sequences and direct chemical synthesis. Chemical synthesis methods can include, for example, the phospho di- or tri-ester method, the diethylphosphoramidate method and the solid support method disclosed in U.S. Pat. No. 4,458,066.

Primers can be labeled, if desired, by incorporating detectable moieties by for instance spectroscopic, fluorescence, photochemical, biochemical, immunochemical, or chemical moieties.

The PCR method is well described in handbooks and known to the skilled person. After amplification by PCR, target polynucleotides can be detected by hybridization with a probe polynucleotide which forms a stable hybrid with that of the target sequence under stringent to moderately stringent hybridization and wash conditions. If it is expected that the probes are essentially completely complementary (i.e., about 99% or greater) to the target sequence, stringent conditions can be used. If some mismatching is expected, for example if variant strains are expected with the result that the probe will not be completely complementary, the stringency of hybridization can be reduced. In some embodiments, conditions are chosen to rule out non-specific/adventitious binding. Conditions that affect hybridization, and that select against non-specific binding are known in the art, and are described in, for example, Sambrook & Russell (2001). *Molecular Cloning: A Laboratory Manual, Third Edition*, Cold Spring Harbor Laboratory Press, Cold Spring Harbor, N.Y., United States of America. Generally, lower salt concentration and higher temperature hybridization and/or washes increase the stringency of hybridization conditions.

Continuing, the term "probe" refers to a single-stranded oligonucleotide sequence that will form a hydrogen-bonded duplex with a complementary sequence in a target nucleic acid sequence analyte or its cDNA derivative.

Figure 1B:
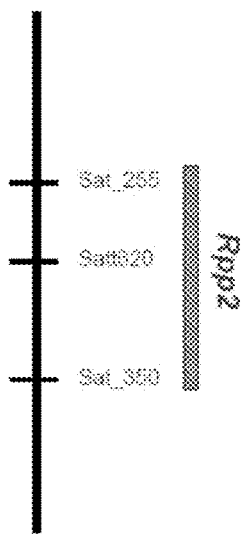
Figure 1C:
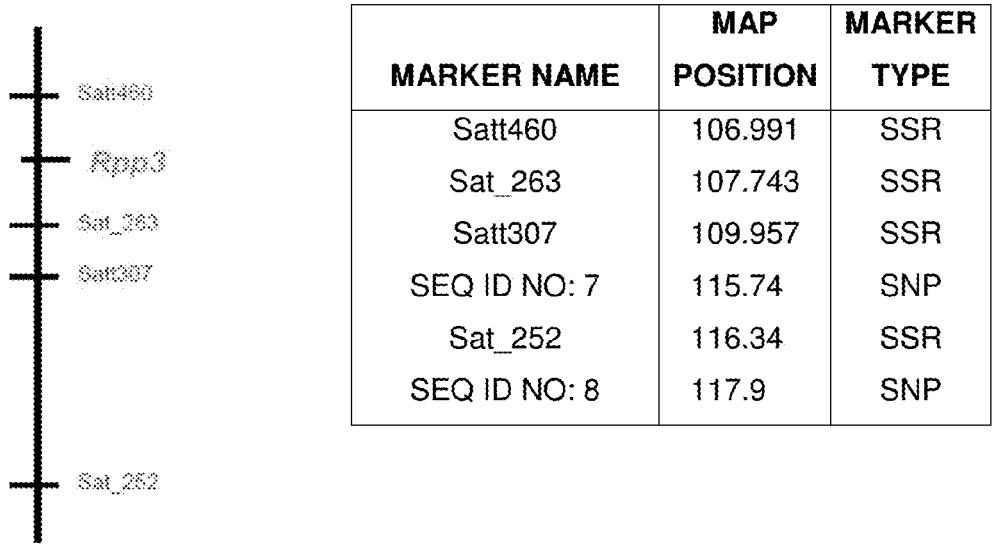
Figure 1D:
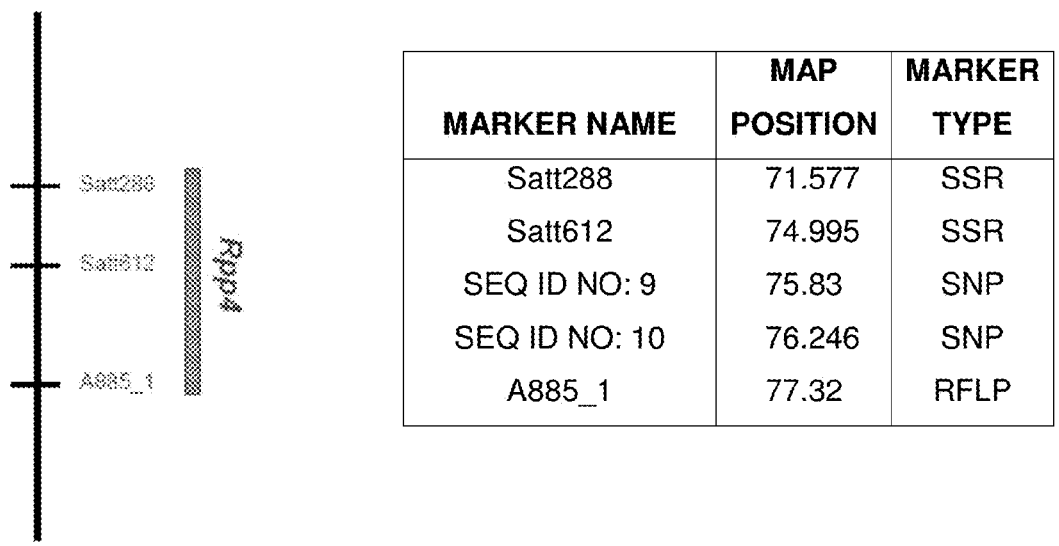
Figure 1E:
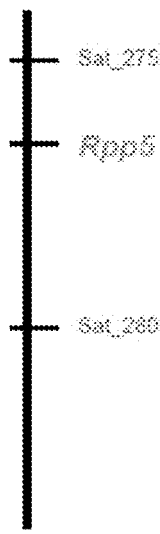

As used herein, the terms "Rpp1", "Rpp2", "Rpp3", "Rpp4", and "Rpp5" refer to loci that have been associated with SBR resistance as defined by the markers defined herein. For the purposes of the instant disclosure, these loci are said to be present on *Glycine* linkage groups G, J, C2, G, and N, and linked to the markers depicted in FIGS. 1A-1E, respectively.

As used herein, the term "quantitative trait locus" (QTL; plural quantitative trait loci; QTLs) refers to a genetic locus (or loci) that controls to some degree a numerically representable trait that, in some embodiments, is continuously distributed. As such, the term QTL is used herein in its art-recognized meaning to refer to a chromosomal region containing alleles (e.g., in the form of genes or regulatory sequences) associated with the expression of a quantitative phenotypic trait. Thus, a QTL "associated with" resistance to SBR refers to one or more regions located on one or more chromosomes and/or in one or more linkage groups that includes at least one gene the expression of which influences a level of resistance and/or at least one regulatory region that controls the expression of one or more genes involved in resistance to SBR. QTLs can be defined by indicating their genetic location in the genome of a specific *Glycine* sp. accession using one or more molecular genomic markers. One or more markers, in turn, indicate a specific locus. Distances between loci are usually measured by the frequency of crossovers between loci on the same chromosome. The farther apart two loci are, the more likely that a crossover will occur between them. Conversely, if two loci are close together, a crossover is less likely to occur between them. Typically, one centiMorgan (cM) is equal to 1% recombination between loci. When a QTL can be indicated by multiple markers, the genetic distance between the endpoint markers is indicative of the size of the QTL.

As used herein, the term "regenerate", and grammatical variants thereof, refers to the production of a plant from tissue culture.

As used herein, the term "resistant" and "resistance" encompass both partial and full resistance to infection (e.g., infection by a pathogen that causes SBR). A susceptible plant can either be non-resistant or have lower levels of resistance to infection relative to a resistant plant. The term is used to include such separately identifiable forms of resistance as "full resistance", "immunity", "intermediate resistance", "partial resistance", and "hypersensitivity".

As used herein, the phrase "stringent hybridization conditions" refers to conditions under which a polynucleotide hybridizes to its target subsequence, typically in a complex mixture of nucleic acids, but to essentially no other sequences. Stringent conditions are sequence-dependent and can be different under different circumstances. Exemplary guidelines for the hybridization of nucleic acids can be found in Tijssen (1993) *in Laboratory Techniques in Biochemistry and Molecular Biology*, Elsevier, New York, N.Y., United States of America; Ausubel et al. (1999) *Short Protocols in Molecular Biology* Wiley, New York, N.Y., United States of America; and Sambrook & Russell, 2001 (supra). Generally, stringent conditions are selected to be about 5-10° C. lower than the thermal melting point (Tm) for the specific sequence at a defined ionic strength pH. The Tm is the temperature (under defined ionic strength, pH, and nucleic acid concentration) at which 50% of the probes complementary to the target hybridize to the target sequence at equilibrium (as the target sequences are present in excess, at Tm, 50% of the probes are occupied at equilibrium). Stringent conditions are those in which the salt concentration is less than about 1.0 M sodium ion, typically about 0.01 to 1.0 M sodium ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Stringent conditions can also be achieved with the addition of destabilizing agents such as formamide. Exemplary stringent hybridization conditions include: 50% formamide, 5×SSC, and 1% SDS, incubating at 42° C.; or 5×SSC, 1% SDS, incubating at 65° C.; with one or more washes in 0.2×SSC and 0.1% SDS at 65° C. For PCR, a temperature of about 36° C. is typical for low stringency amplification, although annealing temperatures can vary between about 32° C. and 48° C. (or higher) depending on primer length.

As used herein, the term "susceptible" refers to a plant having no resistance to the disease resulting in the plant being affected by the disease, resulting in disease symptoms. The term "susceptible" is therefore equivalent to "non-resistant". Alternatively, the term "susceptible" can be employed in a relative context, in which one plant is considered "susceptible" because it is less resistant to a particular pathogen than is a second plant (which in the context of these terms in a relative usage, would be referred to as the "resistant" plant").

II. General Considerations

Previous studies on host resistance to *P. pachyrhizi* have resulted in the identification of the four major resistance genes, Rpp1, Rpp2, Rpp3, and Rpp4, in soybean accessions PI 200492, PI 230970, PI 462312, and PI 459025B, respectively. Three of these genes (Rpp2, Rpp3, and Rpp4) confer a resistant reddish-brown (RB) colored lesion as opposed to the susceptible tan (TAN) colored lesion. Rpp1, on the other hand, confers resistance to some rust isolates. These four genes have been mapped on linkage groups (LGs) G, J, C2, and G, respectively. An RB lesion type resistance gene Rpp?(Hyuuga) from the Japanese cultivar "Hyuuga" has been mapped by to the same region on LG C2 as Rpp3. A fifth gene, Rpp5, was recently identified from PI200456 and mapped on LG N. With the availability of the 7× sequence coverage of the soybean genome made possible by efforts of the U. S. Department of Energy-Joint Genome Institute (DOE-JGI), Rpp1 has been fine mapped to a 23 kb region on scaffold 21 of LG G, and several markers close to this gene have been identified (Hyten et al. (2008) *Theor Appl Genet* 116:945-952).

Resistance conferred by Rpp1, Rpp2, Rpp3, Rpp4, and Rpp5 can be race-specific, and can be overcome by various *P. pachyrhizi* isolates. For example, resistance in soybean lines carrying either Rpp1 or Rpp3 genes failed in Brazil within two years of the establishment of the disease.

The presently disclosed subject matter provides in some embodiments soybean varieties that are resistant to SBR, methods for identifying soybean plants that carry desirable resistance genes, and methods for introducing such desirable resistance genes into soybeans.

III. Plant Breeding

The presently disclosed subject matter provides for better models for marker-assisted breeding (MAB). The presently disclosed subject matter therefore relates to methods of plant breeding and to methods to select plants, in particular soybean plants, particularly cultivated soybean plants as breeder plants for use in breeding programs or cultivated soybean plants for having desired genotypic or potential phenotypic properties, in particular related to producing valuable soybeans, also referred to herein as commercially valuable plants. Herein, a cultivated plant is defined as a plant being purposely selected or having been derived from a plant having been purposely selected in agricultural or horticultural practice for having desired genotypic or potential phenotypic properties, for example a plant obtained by inbreeding.

The presently disclosed subject matter thus also provides methods for selecting a plant of the genus *Glycine* exhibiting resistance towards SBR comprising detecting in the plant the presence of one or more resistance alleles as defined herein. In an exemplary embodiment of the presently disclosed methods for selecting such a plant, the method comprises providing a sample of genomic DNA from a soybean plant; and (b) detecting in the sample of genomic DNA at least one molecular marker associated with resistance to SBR. In some embodiments, the detecting can comprise detecting one or more SNPs that are associated with resistance to SBR.

The providing of a sample of genomic DNA from a soybean plant can be performed by standard DNA isolation methods well known in the art.

The detecting of a molecular marker can in some embodiments comprise the use of one or more sets of primer pairs that can be used to produce one or more amplification products that are suitable markers for one of the SNPs. Such a set of primers can comprise, in some embodiments, nucleotide sequences as set forth in SEQ ID NOs: 14-81.

In some embodiments, the detecting of a molecular marker can comprise the use of a nucleic acid probe having a base sequence that is substantially complementary to the nucleic acid sequence defining the molecular marker and which nucleic acid probe specifically hybridizes under stringent conditions with a nucleic acid sequence defining the molecular marker. A suitable nucleic acid probe can for instance be a single strand of the amplification product corresponding to the marker. In some embodiments, the detecting of a molecular marker is designed to discriminate whether a particular allele of an SNP is present or absent in a particular plant.

The presently disclosed methods can also include detecting an amplified DNA fragment associated with the presence of a particular allele of an SNP. In some embodiments, the amplified fragment associated with a particular allele of an SNP has a predicted length or nucleic acid sequence, and detecting an amplified DNA fragment having the predicted length or the predicted nucleic acid sequence is performed such that the amplified DNA fragment has a length that corresponds (plus or minus a few bases; e.g., a length of one, two or three bases more or less) to the expected length as based on a similar reaction with the same primers with the DNA from the plant in which the marker was first detected or the nucleic acid sequence that corresponds (i.e., has a homology of in some embodiments more than 80%, in some embodiments more than 90%, in some embodiments more than 95%, in some embodiments more than 97%, and in some embodiments more than 99%) to the expected sequence as based on the sequence of the marker associated with that SNP in the plant in which the marker was first detected. Upon a review of the instant disclosure, one of ordinary skill in the art would appreciate that markers (e.g., SNP alleles) that are absent in resistant plants, while they were present in the susceptible parent(s) (so-called trans-markers), can also be useful in assays for detecting resistance among offspring plants.

The detecting of an amplified DNA fragment having the predicted length or the predicted nucleic acid sequence can be performed by any of a number or techniques, including but not limited to standard gel-electrophoresis techniques or by using automated DNA sequencers. The methods are not described here in detail as they are well known to the skilled person, although exemplary approaches are set forth in the EXAMPLES.

IV. Molecular Markers and SNPs

Molecular markers are used for the visualization of differences in nucleic acid sequences. This visualization can be due to DNA-DNA hybridization techniques after digestion with a restriction enzyme (e.g., an RFLP) and/or due to techniques using the polymerase chain reaction (e.g., STS, SSR/microsatellites, AFLP, and the like). In some embodiments, all differences between two parental genotypes segregate in a mapping population based on the cross of these parental genotypes. The segregation of the different markers can be compared and recombination frequencies can be calculated. Methods for mapping markers in plants are disclosed in, for example, Glick & Thompson (1993) *Methods in Plant Molecular Biology and Biotechnology*, CRC Press, Boca Raton, Fla., United States of America; Zietkiewicz et al. (1994) *Genomics* 20:176-183.

The recombination frequencies of molecular markers on different chromosomes and/or in different linkage groups are generally 50%. Between molecular markers located on the same chromosome or in the same linkage group, the recombination frequency generally depends on the distance between the markers. A low recombination frequency typically corresponds to a low genetic distance between markers on a chromosome. Comparing all recombination frequencies results in the most logical order of the molecular markers on the chromosomes or in the linkage groups. This most logical order can be depicted in a linkage map. A group of adjacent or contiguous markers on the linkage map that is associated with an increased level of resistance to a disease; e.g., to a reduced incidence of acquiring the disease upon infectious contact with the disease agent and/or a reduced lesion growth rate upon establishment of infection, can provide the position of a locus associated with resistance to that disease.

The markers disclosed herein can be used in various aspects of the presently disclosed subject matter as set forth hereinbelow. Aspects of the presently disclosed subject matter are not to be limited to the use of the markers identified herein, however. It is stressed that the aspects can also make use of markers not explicitly disclosed herein or even yet to be identified. Other than the genetic unit "gene", on which the phenotypic expression depends on a large number of factors that cannot be predicted, the genetic unit "QTL" denotes a region of the genome that is directly related to a phenotypic quantifiable trait.

The markers provided by the presently disclosed subject matter can be used for detecting the presence of one or more SBR resistance alleles of the presently disclosed subject matter in a suspected SBR-resistant soybean plant, and can therefore be used in methods involving marker-assisted breeding and selection of SBR resistant soybean plants. In some embodiments, detecting the presence of a particular allele of an SNP of the presently disclosed subject matter is performed with at least one of the markers for the resistance loci defined herein. The presently disclosed subject matter therefore relates in another aspect to a method for detecting the presence of a particular allele associated with SBR resistance, comprising detecting the presence of a nucleic acid sequence of the SNP in a suspected SBR-resistant soybean plant, which presence can be detected by the use of the disclosed markers and oligonucleotides.

The nucleotide sequence of an SNP of the presently disclosed subject matter can for instance be resolved by determining the nucleotide sequence of one or more markers associated with the SNP and designing internal primers for the marker sequences that can be used to determine which allele of the SNP is present in the plant.

In embodiments of such methods for detecting the presence of an SNP in a suspected SBR-resistant soybean plant, the method can also comprise providing a oligonucleotide or polynucleotide capable of hybridizing under stringent hybridization conditions to a particular nucleic acid sequence of an SNP, in some embodiments selected from the SNPs disclosed herein, contacting the oligonucleotide or polynucleotide with genomic nucleic acid (or a fragment thereof, including, but not limited to a restriction fragment thereof) of a suspected SBR-resistant soybean plant, and determining the presence of specific hybridization of the oligonucleotide or polynucleotide to the genomic nucleic acid (or the fragment thereof).

In some embodiments, the method is performed on a nucleic acid sample obtained from the suspected SBR-resistant soybean plant, although in situ hybridization methods can also be employed. Alternatively, one of ordinary skill in the art can design specific hybridization probes or oligonucleotides capable of hybridizing under stringent hybridization conditions to the nucleic acid sequence of the allele associated with SBR resistance and can use such hybridization probes in methods for detecting the presence of an SNP allele disclosed herein in a suspected SBR-resistant soybean plant.

V. Production of SBR-Resistant Soybean Plants

The presently disclosed subject matter also relates to methods for producing an SBR-resistant soybean plant comprising performing a method for detecting the presence of an allele associated with resistance to SBR in a donor soybean plant according to the presently disclosed subject matter as described above, and transferring a nucleic acid sequence comprising at least one allele thus detected, or an SBR resistance-conferring part thereof, from the donor plant to an SBR-susceptible recipient soybean plant. The transfer of the nucleic acid sequence can be performed by any of the methods described herein.

An exemplary embodiment of such a method comprises the transfer by introgression of the nucleic acid sequence from an SBR-resistant donor soybean plant into an SBR-susceptible recipient soybean plant by crossing the plants. This transfer can thus suitably be accomplished by using traditional breeding techniques. SBR-resistance loci are introgressed in some embodiments into commercial soybean varieties using marker-assisted selection (MAS) or marker-assisted breeding (MAB). MAS and MAB involves the use of one or more of the molecular markers for the identification and selection of those offspring plants that contain one or more of the genes that encode for the desired trait. In the context of the presently disclosed subject matter, such identification and selection is based on selection of SNP alleles of the presently disclosed subject matter or markers associated therewith. MAB can also be used to develop near-isogenic lines (NIL) harboring the QTL of interest, allowing a more detailed study of each QTL effect and is also an effective method for development of backcross inbred line (BIL) populations. Soybean plants developed according to these embodiments can advantageously derive a majority of their traits from the recipient plant, and derive SBR resistance from the donor plant.

As discussed hereinabove, traditional breeding techniques can be used to introgress a nucleic acid sequence encoding SBR resistance into an SBR-susceptible recipient soybean plant. In some embodiments, a donor soybean plant that exhibits resistance to SBR and comprising a nucleic acid sequence encoding SBR resistance is crossed with an SBR-susceptible recipient soybean plant that in some embodiments exhibits commercially desirable characteristics, such as, but not limited to, disease resistance, insect resistance, valuable nutritional characteristics, and the like. The resulting plant population (representing the F1 hybrids) is then self-pollinated and set seeds (F2 seeds). The F2 plants grown from the F2 seeds are then screened for resistance to SBR. The population can be screened in a number of different ways.

First, the population can be screened using a traditional disease screen. Such disease screens are known in the art. In some embodiments, a quantitative bioassay is used. Second, marker-assisted breeding can be performed using one or more of the herein-described molecular markers to identify those progeny that comprise a nucleic acid sequence encoding for SBR resistance. Other methods, referred to hereinabove by methods for detecting the presence of an allele associated with SBR resistance, can be used. Also, marker-assisted breeding can be used to confirm the results obtained from the quantitative bioassays, and therefore, several methods can also be used in combination.

Inbred SBR-resistant soybean plant lines can be developed using the techniques of recurrent selection and backcrossing, selfing, and/or dihaploids, or any other technique used to make parental lines. In a method of recurrent selection and backcrossing, SBR resistance can be introgressed into a target recipient plant (the recurrent parent) by crossing the recurrent parent with a first donor plant, which differs from the recurrent parent and is referred to herein as the "non-recurrent parent". The recurrent parent is a plant that is non-resistant or has a low level of resistance to SBR and possesses commercially desirable characteristics, such as, but not limited to (additional) disease resistance, insect resistance, valuable nutritional characteristics, and the like. In some embodiments, the non-recurrent parent exhibits SBR resistance and comprises a nucleic acid sequence that encodes SBR resistance. The non-recurrent parent can be any plant variety or inbred line that is cross-fertile with the recurrent parent.

The progeny resulting from a cross between the recurrent parent and non-recurrent parent are backcrossed to the recurrent parent. The resulting plant population is then screened for the desired characteristics, which screening can occur in a number of different ways. For instance, the population can be screened using phenotypic pathology screens or quantitative bioassays as known in the art. Alternatively, instead of using bioassays, MAB can be performed using one or more of the hereinbefore described molecular markers, hybridization probes, or polynucleotides to identify those progeny that comprise a nucleic acid sequence encoding SBR resistance. Also, MAB can be used to confirm the results obtained from the quantitative bioassays. In some embodiments, the markers defined herein are suitable to select proper offspring plants by genotypic screening.

Following screening, the F1 hybrid plants that exhibit an SBR-resistant phenotype or, in some embodiments, genotype and thus comprise the requisite nucleic acid sequence encoding SBR resistance, are then selected and backcrossed to the recurrent parent for a number of generations in order to allow for the soybean plant to become increasingly inbred. This process can be performed for two, three, four, five, six, seven, eight, or more generations. In principle, the progeny resulting from the process of crossing the recurrent parent with the SBR-resistant non-recurrent parent are heterozygous for one or more genes that encode SBR resistance.

In general, a method of introducing a desired trait into a hybrid soybean variety can comprise:
(a) crossing an inbred soybean parent with another soybean plant that comprises one or more desired traits, to produce F1 progeny plants, wherein the desired trait is SBR resistance;
(b) selecting the F1 progeny plants that have the desired trait to produce selected F1 progeny plants, in some embodiments using molecular markers as defined herein;
(c) backcrossing the selected progeny plants with the inbred soybean parent plant to produce backcross progeny plants;
(d) selecting for backcross progeny plants that have the desired trait and morphological and physiological characteristics of the inbred soybean parent plant, wherein the selection comprises the isolation of genomic DNA and testing the DNA for the presence of at least one molecular marker for SBR resistance, in some embodiments as described herein;
(e) repeating steps (c) and (d) two or more times in succession to produce selected third or higher backcross progeny plants;
(f) optionally selfing selected backcross progeny in order to identify homozygous plants; and
(g) crossing at least one of the backcross progeny or selfed plants with another soybean parent plant to generate a hybrid soybean variety with the desired trait and all of the morphological and physiological characteristics of hybrid soybean variety when grown in the same environmental conditions.

As indicated, the last backcross generation can be selfed in order to provide for homozygous pure breeding (inbred) progeny for SBR resistance. Thus, the result of recurrent selection, backcrossing, and selfing is the production of lines that are genetically homogenous for the genes associated with SBR resistance, and in some embodiments as well as for other genes associated with traits of commercial interest.

VI. SBR-Resistant Soybean Plants and Seeds

The development of a hybrid soybean variety in a soybean plant breeding program can, in some embodiments, involve three steps: (1) the selection of plants from various germplasm pools for initial breeding crosses; (2) the selfing of the selected plants from the breeding crosses for several generations to produce a series of inbred lines, which, individually breed true and are highly uniform; and (3) crossing a selected variety with an different variety to produce the hybrid progeny (F1). After a sufficient amount of inbreeding successive filial generations will merely serve to increase seed of the developed inbred. In some embodiments, an inbred line comprises homozygous alleles at about 95% or more of its loci.

A SBR-resistant soybean plant, or a part thereof, obtainable by a method of the presently disclosed subject matter is an aspect of the presently disclosed subject matter.

The SBR-resistant soybean plants of the presently disclosed subject matter, or part thereof, can be heterozygous or homozygous for the resistance traits (in some embodiments, homozygous). Although the SBR resistance loci of the presently disclosed subject matter, as well as resistance-conferring parts thereof, can be transferred to any plant in order to provide for an SBR-resistant plant, the methods and plants of the presently disclosed subject matter are in some embodiments related to plants of the genus *Glycine*.

The SBR-resistant soybean lines described herein can be used in additional crossings to create SBR-resistant plants. For example, a first SBR-resistant soybean plant of the presently disclosed subject matter can be crossed with a second soybean plant possessing commercially desirable traits such as, but not limited to, disease resistance, insect resistance, desirable nutritional characteristics, and the like. In some embodiments, this second soybean line is itself SBR-resistant. In some embodiments, this line is heterozygous or homozygous for one or more of the disclosed SBR resistance loci, in order for one or more of these traits to be expressed in the hybrid offspring plants.

Another aspect of the presently disclosed subject matter relates to a method of producing seeds that can be grown into SBR-resistant soybean plants. In some embodiments, the method comprises providing a SBR-resistant soybean plant of the presently disclosed subject matter, crossing the SBR-resistant plant with another soybean plant, and collecting seeds resulting from the cross, which when planted, produce SBR-resistant soybean plants.

In some embodiments, the method comprises providing a SBR-resistant soybean plant of the presently disclosed subject matter, crossing the SBR-resistant plant with a soybean plant, collecting seeds resulting from the cross, regenerating the seeds into plants, selecting SBR-resistant plants by any of the methods described herein, self-pollinating the selected plants for a sufficient number of generations to obtain plants that are fixed for an allele associated with SBR-resistance in the plants, backcrossing the plants thus produced with soybean plants having desirable phenotypic traits for a sufficient number of generations to obtain soybean plants that are SBR-resistant and have desirable phenotypic traits, and collecting the seeds produced from the plants resulting from the last backcross, which when planted, produce soybean plants which are SBR-resistant.

VII. Other Applications

With the use of these SNPs for breeding new soybean lines, a system for developing germplasm that has more than one mode of action against the fungus is made possible. The use of this dual mode of action will assist in inhibiting the fungus from developing resistance. Additionally, a regime for inhibiting fungal resistance can include a number of different modes of action. The different modes of action in an inhibiting fungus method could be through germplasm or seed treatments or chemical applications. A system for inhibiting fungal resistance includes germplasm with one or more vertical resistant traits, and/or germplasm with one or more horizontal tolerance traits with the possible options of including a seed treatment that is active against the fungus, and/or an antifungal spray. Antifungal sprays or treatments can include known antifungal compounds for this fungus but can also include glufosinate or glyphosate sprays, separate or in combination which also have an antifungal affect.

The regime for inhibiting antifungal resistance is very important for the continued effectiveness of germplasm resistance and chemical activity. There are areas in which soybeans are presently produced which have fungal isolates that are no longer negatively affected by at least two of the known Rpp resistance alleles. The ability of these fungal isolates to evolve so quickly could render entire soybean growing areas unprofitable unless the embodiments of the presently disclosed subject matter that provide soybean seeds which are protected by the SNP selected traits for a dual mode of action plus the optional seed treatment, or chemical applications is implemented.

EXAMPLES

The following Examples provide illustrative embodiments. In light of the present disclosure and the general level of skill in the art, those of skill will appreciate that the following Examples are intended to be exemplary only and that numerous changes, modifications, and alterations can be employed without departing from the scope of the presently claimed subject matter.

Example 1

SNP Analysis

There are SSR markers which are associated with soybean rust resistant qualitative and quantitative genes Rpp1, Rpp2, Rpp3, Rpp4, and Rpp5. This SSR information was employed to identify SNP markers that map to the regions of qualitative genes and quantitative trait loci (QTL) regions defined for each of the Rpp1, Rpp2, Rpp3, Rpp4, and Rpp5 genes. The identified SNPs were validated on soybean rust resistant and susceptible lines. Analyses indicated that these SNPs mapped more closely and showed better associations to the Rpp gene than did the SSRs. The information of validated SNPs for soybean rust is new and is used for appropriate breeding programs.

Example 2

SNP Genotyping Data

Molecular markers were identified for the Rpp1, Rpp2, Rpp3, Rpp4, and Rpp5 genes, and the resistance gene first identified in the Japanese cultivar, Hyuuga. Hyten et al., 2007 used PI200492 to map Rpp1 to linkage group (LG) G between the SSR markers Sct_187 and Sat_064. Rpp2 was mapped in PI230970 to the region on LG J between Sat_255 and Satt620. Rpp4 was mapped in PI459025 on LG G between SSR Satt288 and RFLP marker A885_1 (Silva et al., 2008, supra). The cultivar Hyuuga (PI506764) was once thought to contain Rpp3 (the resistance gene contained in PIs 462312 and 459025B), but it is now believed that there are 2 separate rust resistance genes located near each other on LG C2, flanked by SSRs Satt460 and Sat_263. Rpp5 was recently identified in several lines (PI200487, PI200526, PI471904, PI200456) by Garcia et al., 2008, and mapped to LG N in a region flanked by the SSRs Sat_275 and Sat_280. The approximate positions of these genes and various markers are depicted in FIGS. 1A-1E.

The soybean linkage map developed by scientists at the USDA and made publicly available in 2006 can be found through the website of the United States Department of Agriculture (USDA) and is discussed in Choi et al. (2007) *Genetics* 176:685-696. This map was used to locate the flanking SSRs associated with each rust resistance gene and to select SNPs that were mapped within and close to each region. The polymorphism information and genomic sequence on either side of the SNP was used to design PCR-based assays to detect each allele. The sequences with the SNP indicated were either submitted to the Applied Biosystems Inc. (ABI; Foster City, Calif., United States of America) Assay-by-Design service for creation of custom TAQMAN® (Applied Biosystems Inc., Foster City, Calif., United States of America) based assays, or assays were manually designed using the ABI software PRIMER EXPRESS®. Similarly, TAQMAN® assays can be designed using software available from Biosearch Technologies (Novato, Calif., United States of America).

A goal of the SNP assay was to be able to determine which polymorphism(s), or allele(s), is/are present in the genome of any given soybean line, and ultimately to permit the selection of preferred allele(s) (i.e., rust resistant gene(s)), in a marker-assisted breeding program. A total of 17 SNPs were identified; four for Rpp1, five for Rpp2, three for Rpp?(Hyuuga), two for Rpp4, and three for Rpp5. A total of 18 screening panel DNAs isolated from resistant lines (PI547875; PI200492; PI594538A; PI368039; PI547878; PI230970; PI224270; PI462312; PI578457A; PI518772; PI628932; PI506764; PI547879; PI459025B; PI200456; PI200526; PI200487; and PI471904) were used for the assays.

Example 3

Allelic Discrimination Assays

In allelic discrimination assays, a PCR assay included a forward and reverse primer and a specific, fluorescent, dye-labeled probe for each of two alleles for a given SNP. The probes contained different fluorescent reporter dyes (VIC®; Applied Biosystems, Inc., Foster City, Calif., United States of America; and 6-carboxyfluorescein-aminohexyl amidite (FAM), or N-TET-6-Aminohexanol (TET) and FAM) to differentiate the amplification of each allele. A non-fluorescent quencher on each probe suppressed the fluorescence until amplification by PCR. During PCR, each probe annealed specifically to complementary sequences between the forward and reverse primer sites. Taq polymerase then cleaved the probes that were hybridized to each allele. Cleavage separated the reporter dye from the quencher, which resulted in increased fluorescence by the reporter dye.

Thus, the fluorescent signals generated by PCR amplification indicated that one or both alleles were present in the sample. In addition to the non-fluorescent quencher, the probes also contained a minor groove binder at the 3' end which resulted in increased melting temperatures (Tm), thereby allowing high specificity with the use of shorter oligos. These probes therefore exhibited greater Tm differences when hybridized to matched and mismatched templates, which provided more accurate allelic discriminations. Probes of this type were manufactured at either ABI (MGB™ quencher) or Biosearch Technologies (BHQ-PLUS™ quencher). At the end of PCR thermal cycling, fluorescence of the two reporter dyes was measured on an ABI 7900. An increase in fluorescence for one dye only indicated homozygosity for the corresponding allele. An increase in both fluorescent signals indicated heterozygosity.

Exemplary starting lines and haplotypes determined using this method are presented in Tables 3-8. In Tables 3-8, "H" indicates that the line was heterozygous at that position, and "-" indicates that the nucleotide at that position was not determined

TABLE 3

SNP Screening Panel

| Line | Name | Origin | Source of Seed | Resistance |
|---|---|---|---|---|
| PI547875 | L85-2378 | Developed in Illinois, USA | GRIN[1] | Rpp1 |
| PI200492 | | | GRIN | Rpp1 |
| PI594538A | | | GRIN | Rpp1-b |
| PI368039 | Tainung No. 4 | | GRIN | Rpp1 |
| PI547878 | L86-1752 | Developed in Illinois, USA | GRIN | Rpp2 |
| PI230970 | | | GRIN | Rpp2 |
| PI224270 | | | GRIN | Rpp2 |
| PI462312 | Ankur | | GRIN | Rpp3 |
| PI578457A | | | GRIN | Rpp3 |
| PI 518772 | | | GRIN | Rpp3 |
| PI 628932 | | | GRIN | Rpp3 |
| PI506764 | | | GRIN | Rpp? (Hyuuga) |
| PI547879 | L87-0482 | Developed in Illinois, USA | GRIN | Rpp4 |
| PI459025B | (Bing nan) | | GRIN | Rpp4 |
| PI200456 | | | GRIN | Rpp5 |
| PI200526 | | | GRIN | Rpp5 |
| PI200487 | Kinoshita | | GRIN | Rpp5 |
| PI471904 | L85-2378 | Developed in Illinois, USA | GRIN | Rpp5 |

[1]Germplasm Resources Information Network, Agricultural Research Service, United States Department of Agriculture, Beltsville, Maryland, United States of America.

TABLE 4

SNP Genotyping Data - Detailed for Rpp1

| | | | SEQ ID NO: 1 | SEQ ID NO: 2a | SEQ ID NO: 2b | SEQ ID NO: 3 |
|---|---|---|---|---|---|---|
| | | | | Linkage Group | | |
| SPIRIT | | | G | G | G | G |
| | | | | Map Position (cM) | | |
| Material ID | ABBRC | LOCUS | 100.921 Rpp1 | 101.849 Rpp1 | 101.849 Rpp1 | 103.63 Rpp1 |
| PI547875 | L85-2378 | Rpp1 | A | G | T | T |
| PI200492 | | Rpp1 | A | G | T | T |
| PI594538A | | Rpp1-b | A | G | T | T |
| PI368039 | Tainung No. 4 | Rpp1 | A | G | T | T |
| PI547878 | L86-1752 | Rpp2 | G | A | C | C |
| PI230970 | | Rpp2 | G | G | C | C |
| PI224270 | | Rpp2 | G | G | C | C |
| PI462312 | Ankur | Rpp3 | G | A | C | C |
| PI578457A | | Rpp3 | A | — | T | C |

TABLE 4-continued

SNP Genotyping Data - Detailed for Rpp1

| SPIRIT Material ID | ABBRC | LOCUS | SEQ ID NO: 1 Linkage Group G Map Position (cM) 100.921 Rpp1 | SEQ ID NO: 2a G 101.849 Rpp1 | SEQ ID NO: 2b G 101.849 Rpp1 | SEQ ID NO: 3 G 103.63 Rpp1 |
|---|---|---|---|---|---|---|
| PI 518772 | | Rpp3 | G | A | C | C |
| PI 628932 | | Rpp3 | G | A | C | C |
| PI506764 | | Rpp? (Hyuuga) | G | G | C | C |
| PI547879 | L87-0482 | Rpp4 | G | A | C | C |
| PI459025B | (Bing nan) | Rpp4 | G | G | T | C |
| PI200456 | | Rpp5 | G | G | T | C |
| PI200526 | | Rpp5 | H | G | T | C |
| PI200487 | Kinoshita | Rpp5 | A | G | T | C |
| PI471904 | | Rpp5 | A | G | T | C |

TABLE 5

SNP Genotyping Data - Detailed for Rpp2

| SPIRIT Material ID | ABBRC | LOCUS | SEQ ID NO: 4a Linkage Group J Map Position (cM) 49.858 Rpp2 | SEQ ID NO: 4b J 49.858 Rpp2 | SEQ ID NO: 5a J 57.697 Rpp2 | SEQ ID NO: 5b J 57.697 Rpp2 | SEQ ID NO: 6 J 60.927 Rpp2 |
|---|---|---|---|---|---|---|---|
| PI547875 | L85-2378 | Rpp1 | G | G | C | T | G |
| PI200492 | | Rpp1 | G | G | C | T | A |
| PI594538A | | Rpp1-b | G | G | C | T | A |
| PI368039 | Tainung No. 4 | Rpp1 | G | G | C | T | A |
| PI547878 | L86-1752 | Rpp2 | G | G | C | T | G |
| PI230970 | | Rpp2 | G | G | A | T | A |
| PI224270 | | Rpp2 | G | G | A | A | A |
| PI462312 | Ankur | Rpp3 | G | G | C | T | H |
| PI578457A | | Rpp3 | G | G | C | T | A |
| PI 518772 | | Rpp3 | G | G | H | T | A |
| PI 628932 | | Rpp3 | G | G | C | T | H |
| PI506764 | | Rpp? (Hyuuga) | G | G | A | A | A |
| PI547879 | L87-0482 | Rpp4 | G | G | C | T | G |
| PI459025B | (Bing nan) | Rpp4 | G | G | C | T | A |
| PI200456 | | Rpp5 | G | G | A | T | G |
| PI200526 | | Rpp5 | G | G | H | H | A |
| PI200487 | Kinoshita | Rpp5 | G | G | A | A | A |
| PI471904 | | Rpp5 | G | G | A | A | A |

TABLE 6

SNP Genotyping Data - Detailed for Rpp3

| SPIRIT Material ID | ABBRC | LOCUS | SEQ ID NO: 7 C2 115.71 Rpp3 and Rpp? (Hyuuga) | SEQ ID NO: 8a C2 117.9 Rpp3 and Rpp? (Hyuuga) | SEQ ID NO: 8b C2 117.9 Rpp3 and Rpp? (Hyuuga) |
|---|---|---|---|---|---|
| PI547875 | L85-2378 | Rpp1 | T | T | G |
| PI200492 | | Rpp1 | C | T | G |
| PI594538A | | Rpp1-b | C | T | G |
| PI368039 | Tainung No. 4 | Rpp1 | C | T | G |
| PI547878 | L86-1752 | Rpp2 | T | T | G |
| PI230970 | | Rpp2 | C | T | G |
| PI224270 | | Rpp2 | C | C | A |
| PI462312 | Ankur | Rpp3 | C | T | G |
| PI578457A | | Rpp3 | C | T | G |
| PI 518772 | | Rpp3 | T | C | A |
| PI 628932 | | Rpp3 | C | T | G |
| PI506764 | | Rpp? (Hyuuga) | C | C | A |
| PI547879 | L87-0482 | Rpp4 | T | T | G |
| PI459025B | (Bing nan) | Rpp4 | C | T | G |
| PI200456 | | Rpp5 | C | T | G |
| PI200526 | | Rpp5 | C | H | G |
| PI200487 | Kinoshita | Rpp5 | C | T | G |
| PI471904 | | Rpp5 | C | T | G |

TABLE 7

SNP Genotyping Data - Detailed for Rpp4

| SPIRIT Material ID | ABBRC | LOCUS | SEQ ID NO: 9 G 75.83 Rpp4 | SEQ ID NO: 10 G 76.246 Rpp4 |
|---|---|---|---|---|
| PI547875 | L85-2378 | Rpp1 | C | A |
| PI200492 | | Rpp1 | T | C |
| PI594538A | | Rpp1-b | T | C |
| PI368039 | Tainung No. 4 | Rpp1 | T | C |
| PI547878 | L86-1752 | Rpp2 | C | A |
| PI230970 | | Rpp2 | T | C |
| PI224270 | | Rpp2 | C | A |
| PI462312 | Ankur | Rpp3 | T | A |
| PI578457A | | Rpp3 | T | C |
| PI 518772 | | Rpp3 | T | C |
| PI 628932 | | Rpp3 | C | A |
| PI506764 | | Rpp? (Hyuuga) | C | C |
| PI547879 | L87-0482 | Rpp4 | T | C |
| PI459025B | (Bing nan) | Rpp4 | T | C |
| PI200456 | | Rpp5 | T | A |
| PI200526 | | Rpp5 | C | H |
| PI200487 | Kinoshita | Rpp5 | T | C |
| PI471904 | | Rpp5 | T | C |

TABLE 8

SNP Genotyping Data - Detailed for Rpp5

| SPIRIT Material ID | ABBRC | LOCUS | SEQ ID NO: 11 N 34.26 Rpp5 | SEQ ID NO: 12 N 34.27 Rpp5 | SEQ ID NO: 13 N 38.8 Rpp5 |
|---|---|---|---|---|---|
| PI547875 | L85-2378 | Rpp1 | A | T | A |
| PI200492 | | Rpp1 | G | A | G |
| PI594538A | | Rpp1-b | A | T | G |
| PI368039 | Tainung No. 4 | Rpp1 | A | T | G |
| PI547878 | L86-1752 | Rpp2 | A | T | G |
| PI230970 | | Rpp2 | A | T | A |
| PI224270 | | Rpp2 | A | T | G |
| PI462312 | Ankur | Rpp3 | G | A | G |
| PI578457A | | Rpp3 | — | H | G |
| PI 518772 | | Rpp3 | H | H | H |
| PI 628932 | | Rpp3 | A | T | A |
| PI506764 | | Rpp? (Hyuuga) | A | T | G |
| PI547879 | L87-0482 | Rpp4 | A | T | G |
| PI459025B | (Bing nan) | Rpp4 | A | T | A |
| PI200456 | | Rpp5 | A | T | G |
| PI200526 | | Rpp5 | G | H | G |
| PI200487 | Kinoshita | Rpp5 | A | T | G |
| PI471904 | | Rpp5 | A | T | A |

Example 4

TAQMAN® Validation

To validate TAQMAN® allelic discrimination assays for association with disease resistance or tolerance, plants were selected based on their known phenotypic status and compared to the genotype at the specific SNP location. DNA isolated from leaf tissue of seedlings 7-10 days after planting was diluted in TE buffer and stored at 4° C. until used in PCR reactions as described below.

PCR was set up in 5 µl final volumes according to the following formula:

| Reagent | Stock concentration | Per rxn (µl) | For 96 samples (µl) | Final concentration |
|---|---|---|---|---|
| 2X Master Mix* | 2X | 2.5 | 296.88 | 1X |
| AbD primer/probe mix (80x) | 40x | .0625 | 6 | 0.5x |
| PCR-quality H2O | — | 2.44 | 234.24 | — |
| DNA (dried in 384) | 4.5 ng/µl | 4 | — | 3.6 ng/µl (18 ng) |
| Final Volume (µl) | | 5.00 | 357.44 | |

*The Master Mix was JUMPSTART ™ Taq READYMIX ™ (Sigma Catalogue No. 2893; Sigma Chemical Co., St. Louis, Missouri, United States of America), a premix of all the components, including nucleotides and Taq polymerase (but not primers and/or probes) necessary to perform a PCT reaction. Before use, 1375 µl of 1.0M MgCl₂ (Sigma Catalogue No. M1028) and 250 µl of 300 µM Sulforhodamine 101 (Sigma Catalogue No. S7635; ROX) were added to a 125 mL bottle of JUMPSTART ™ Taq READYMIX ™.

PCR plates were placed in an ABI 9700 thermal cycler and the following program was run: an initial denaturation of 50° C. for 2 minutes followed by 95° C. for 10 minutes; 40 cycles of 95° C. for 15 seconds/60° C. for 1 minute; and a final elongation of 72° C. for 5 minutes. After the cycling, the samples were incubated at 4° C. until needed.

The ABI 7900 Sequence Detection System (or TAQ-MAN®) was used to visualize the results of an allelic discrimination (SNP) assay. Using the Sequence Detection System (SDS) software, allele calls were made based on the fluorescence for the two dyes measured in each sample.

It will be understood that various details of the presently disclosed subject matter may be changed without departing from the scope of the presently disclosed subject matter. Furthermore, the foregoing description is for the purpose of illustration only, and not for the purpose of limitation.

What is claimed is:

1. A method for producing a soybean rust (SBR) resistant soybean plant, the method comprising the steps of:

(a) isolating one or more nucleic acids from a plurality of soybean plants;

(b) genotyping said one or more nucleic acid for the presence of a marker associated with SBR resistance located within a chromosome interval, wherein said chromosome interval is located on soybean LG G and is defined by and comprises map positions 75.83 cM to 76.246 cM and wherein said chromosome interval further comprises a T corresponding to position 147 of SEQ ID NO: 9;

(c) selecting a first soybean plant on the basis of the presence of the marker genotyped in (b);

(d) crossing the first soybean plant of (c) with a second soybean plant not having said chromosome interval;

(e) collecting seed from the cross of (d); and (f) growing a progeny soybean plant from the seed of (e), wherein said progeny soybean plant comprises in its genome said chromosome interval thereby producing a SBR resistant soybean plant.

2. The method of claim 1, wherein said chromosome interval comprises a C at position 205 of SEQ ID NO: 10.

3. The method of claim 1, wherein the genotyping in (b) comprises amplifying a marker locus or a portion of the marker locus and detecting the resulting amplified marker amplicon.

4. The method of claim 3, wherein the amplifying comprises: (a) admixing an amplification primer or amplification primer pair with a nucleic acid isolated from the first *Glycine max* plant or germplasm, wherein the primer or primer pair is complementary or partially complementary to at least a portion of the marker locus, and is capable of initiating DNA polymerization by a DNA polymerase using the soybean nucleic acid as a template; and (b) extending the primer or primer pair in a DNA polymerization reaction comprising a DNA polymerase and a template nucleic acid to generate at least one amplicon.

5. The method of claim 4, wherein the nucleic acid is selected from DNA and RNA.

6. The method of claim 5, wherein the amplifying comprises employing a polymerase chain reaction (PCR) or ligase chain reaction (LCR) using a nucleic acid isolated from the first soybean plant or germplasm as a template in the PCR or LCR.

* * * * *